1000

(12) United States Patent
Kim et al.

(10) Patent No.: US 10,772,597 B2
(45) Date of Patent: Sep. 15, 2020

(54) X-RAY APPARATUS AND SYSTEM

(71) Applicant: SAMSUNG ELECTRONICS CO., LTD., Suwon-si (KR)

(72) Inventors: Seung-hoon Kim, Suwon-si (KR);
Si-won Park, Suwon-si (KR);
Hye-kyoung Hong, Seoul (KR);
Jin-beom Hong, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 237 days.

(21) Appl. No.: 16/043,918

(22) Filed: Jul. 24, 2018

(65) Prior Publication Data

US 2018/0325486 A1 Nov. 15, 2018

Related U.S. Application Data

(63) Continuation of application No. 14/962,029, filed on Dec. 8, 2015, now Pat. No. 10,034,649.

(30) Foreign Application Priority Data

Dec. 8, 2014 (KR) .................. 10-2014-0175382

(51) Int. Cl.
*A61B 6/08* (2006.01)
*A61B 6/00* (2006.01)
(Continued)

(52) U.S. Cl.
CPC .................. *A61B 6/54* (2013.01); *A61B 6/06* (2013.01); *A61B 6/544* (2013.01); *A61B 6/08* (2013.01);
(Continued)

(58) Field of Classification Search
CPC .... A61B 6/52; A61B 6/06; A61B 6/08; A61B 6/469; A61B 6/548; A61B 6/00;
(Continued)

(56) References Cited

U.S. PATENT DOCUMENTS 5,396,532 A 3/1995 Aichinger et al.
7,172,340 B2 2/2007 Oota
(Continued)

FOREIGN PATENT DOCUMENTS

DE 198 02 499 A1 7/1999
DE 101 18 183 A1 11/2002
(Continued)

OTHER PUBLICATIONS

Communication dated Jul. 17, 2019 issued by the European Intellectual Property Office in counterpart European Application No. 18213535.0.
(Continued)

*Primary Examiner* — Don K Wong
(74) *Attorney, Agent, or Firm* — Sughrue Mion, PLLC

(57) ABSTRACT

An X-ray apparatus includes a collimator comprising a lamp and configured to adjusting an irradiation region of X-rays radiated from an X-ray source; an image acquirer configured to acquire an object image by imaging an object while the lamp is turned on; and a controller configured to acquire an object distance based on the object image and acquire a thickness of the object based on a detector distance and the object distance. The object distance is a distance between the X-ray source and the object, and the detector distance is a distance between the X-ray source and an X-ray detector.

20 Claims, 32 Drawing Sheets

(51) Int. Cl.
*A61B 6/06* (2006.01)
*G21K 1/04* (2006.01)

(52) U.S. Cl.
CPC ............... *A61B 6/467* (2013.01); *A61B 6/588* (2013.01); *G21K 1/046* (2013.01)

(58) Field of Classification Search
CPC ....... A61B 6/5241; A61B 6/027; A61B 6/032; A61B 6/544
See application file for complete search history.

(56) References Cited

U.S. PATENT DOCUMENTS

| | | | |
|---|---|---|---|
| 7,693,263 | B2 | 4/2010 | Bouvier et al. |
| 8,948,346 | B2 | 2/2015 | Cho et al. |
| 9,008,269 | B2 * | 4/2015 | Wang ................ A61B 6/52 378/146 |
| 2007/0025525 | A1 | 2/2007 | Gilath |
| 2008/0037708 | A1 | 2/2008 | Kuzmanovic |
| 2010/0272344 | A1 | 10/2010 | Ichihara et al. |
| 2012/0039447 | A1 | 2/2012 | Lalena et al. |
| 2014/0140477 | A1 | 5/2014 | Richard et al. |
| 2014/0355735 | A1 | 12/2014 | Choi et al. |

FOREIGN PATENT DOCUMENTS

| | | |
|---|---|---|
| EP | 2 564 787 A1 | 3/2013 |
| JP | 2008-36420 A | 2/2008 |
| JP | 2008-167886 A | 7/2008 |
| JP | 2010-057573 A | 3/2010 |
| KR | 10-2010-0055974 A | 5/2010 |
| KR | 10-2013-0047185 A | 5/2013 |
| WO | 2014/033614 A1 | 3/2014 |

OTHER PUBLICATIONS

Communication issued by the European Patent Office dated Feb. 20, 2018 in counterpart European Patent Application No. 15866489.6.
International Search Report and Written Opinion, issued by International Searching Authority in corresponding International Application No. PCT/KR2015/013183, dated Mar. 10, 2016. (PCT/ISA/220, PCT/ISA/210 & PCT/ISA/237).

* cited by examiner

FIG. 19

| FIRST RELATIONSHIP INFORMATION(40) ||
|---|---|
| SID(41) | REGION SIZE(42) |
| FIRST DISTANCE | FIRST SIZE |
| SECOND DISTANCE | SECOND SIZE |
| THIRD DISTANCE | THIRD SIZE |
| ⋮ | ⋮ |

FIG. 20

| SECOND RELATIONSHIP INFORMATION (60) ||
|---|---|
| THICKNESS INFORMATION(61) | IRRADIATION AMOUNT INFORMATION(62) |
| FIRST THICKNESS | FIRST IRRADIATION AMOUNT |
| SECOND THICKNESS | SECOND IRRADIATION AMOUNT |
| THIRD THICKNESS | THIRD IRRADIATION AMOUNT |
| ⋮ | ⋮ |

X-RAY APPARATUS AND SYSTEM

CROSS-REFERENCE TO RELATED APPLICATION

This application is a Continuation of U.S. application Ser. No. 14/962,029 filed Dec. 8, 2015, which claims benefit from Korean Patent Application No. 10-2014-0175382, filed on Dec. 8, 2014, in the Korean Intellectual Property Office, the disclosures of which are incorporated herein by reference in their entirety.

BACKGROUND

1. Field

The present disclosure relates to an X-ray apparatus and system, and more particularly, to an X-ray apparatus and system that may determine a thickness of an object.

2. Description of the Related Art

X-rays are electromagnetic waves which may generally have a wavelength of 0.01 to 100 angstrom (Å). Because X-rays may be transmitted through an object, X-rays are widely used in medical apparatuses capturing images of the insides of bodies, non-invasive examination devices in various general fields, and the like.

An X-ray apparatus may acquire an X-ray image by transmitting X-rays emitted from an X-ray source through a target, and detecting an intensity difference of the transmitted X-rays by using an X-ray detector. An inner structure of the target may be identified and diagnosis of the object may be performed by using the X-ray image. The X-ray apparatus may be advantageous for conveniently understanding the inner structure of the object by utilizing the fact that a transmission rate of X-rays varies according to a density of the object and an atomic number of atoms that form the object. When X-rays have short wavelengths, the transmission rate increases and images have improved brightness.

SUMMARY

Provided are an X-ray apparatus and system that may determine a thickness of an object.

Additional aspects will be set forth in part in the description which follows and, in part, will be apparent from the description, or may be learned by practice of the presented exemplary embodiments.

According to an aspect of an exemplary embodiment, and X-ray apparatus includes a collimator comprising a lamp, the collimator being configured to adjust an irradiation region of X-rays radiated from an X-ray source; an image acquirer configured to acquire an object image by imaging an object while the lamp illuminates the object; and a controller configured to determine an object distance based on the object image and determine a thickness of the object based on a detector distance and the object distance, wherein the object distance is a distance between the X-ray source and the object, and the detector distance is a distance between the X-ray source and an X-ray detector.

The controller may be further configured to determine, based on the thickness of the object, an irradiation condition, the irradiation condition being information related to an X-ray radiation amount of the X-ray source, and the X-ray apparatus may further include an output interface configured to output the irradiation condition.

The X-ray apparatus may further include an input interface configured to receive X-ray setting information corresponding to the X-ray radiation amount of the X-ray source from a user.

The X-ray source may be configured to radiate X-rays according to the X-ray radiation amount based on the X-ray setting information.

The controller may be further configured to detect in the object image a collimation region illuminated by the lamp, and to acquire the object distance based on a size of the collimation region.

The X-ray apparatus may further include a memory configured to store at least one of first relationship information about a relationship between the object distance and the size of the collimation region, and second relationship information about a relationship between the thickness of the object and the X-ray radiation amount.

The collimator may further include an irradiation window through which X-rays radiated from the X-ray source pass, and the controller may be further configured to adjust a size of the irradiation window to a first size when the object is imaged, and to adjust the size of the irradiation window to a second size when the X-ray source radiates X-rays.

The controller may be further configured to detect a center of the collimation region in the object image, and to acquire the object distance based on a location of the center.

The image acquirer may be further configured to acquire a detector image by imaging the X-ray detector while the object is not between the X-ray source and the X-ray detector and the X-ray detector is illuminated by the lamp, and the controller may be further configured to determine the detector distance based on the detector image.

The X-ray apparatus may further include an input interface configured to receive distance setting information related to the detector distance, and the controller may be further configured to change a location of the X-ray source based on the distance setting information and the detector distance.

The image acquirer may be further configured to acquire a non-illuminated object image by imaging the object while the object is not illuminated by the lamp, and the controller may be further configured to acquire a difference image by comparing the object image and the non-illuminated object image, to detect a collimation region illuminated by light radiated from the lamp from the difference image, and to acquire the object distance based on a size of the collimation region.

According to another aspect of an exemplary embodiment, a workstation configured to control an X-ray apparatus comprising an X-ray source and a collimator includes a communicator configured to receive an object image acquired by imaging an object while a lamp of the collimator illuminates the object, the collimator being configured to adjust an X-ray irradiation region of X-rays radiated from the X-ray source; and a controller configured to determine an object distance based on the object image, and to determine a thickness of the object based on the object distance and a detector distance, wherein the object distance is a distance between the X-ray source and the object, and the detector distance is a distance between the X-ray source and an X-ray detector.

The controller may be further configured to determine, based on the thickness of the object, an irradiation condition, the irradiation condition being information related to an X-ray radiation amount of the X-ray source, and the workstation may further include an output interface configured to output the irradiation condition.

The workstation may further include an input interface configured to receive X-ray setting information corresponding to the X-ray radiation amount of the X-ray source from a user.

The controller may be further configured to control the X-ray source to radiate X-rays according to the X-ray radiation amount based on the X-ray setting information.

The controller may be further configured to detect in the object image a collimation region illuminated by light from the lamp, and to determine the object distance based on a size of the collimation region.

The workstation may further include a memory configured to store at least one from among first relationship information about a relationship between the object distance and the size of the collimation region, and second relationship information about a relationship between the thickness of the object and the X-ray radiation amount.

The collimator may further include an irradiation window through which X-rays radiated from the X-ray source pass, and the controller may be further configured to adjust a size of the irradiation window to a first size when the object is imaged, and to adjust the size of the irradiation window to a second size when the X-ray source radiates X-rays.

According to yet another aspect of an exemplary embodiment, a method of operating an X-ray system includes determining an object distance based on an object image acquired by imaging an object while a lamp of a collimator illuminates the object, wherein the collimator is configured to adjust an X-ray irradiation region of X-rays radiated from an X-ray source; and determining a thickness of the object based on the object distance and a detector distance, wherein the object distance is a distance between the X-ray source and the object, and the detector distance is a distance between the X-ray source and an X-ray detector.

The method may further include: determining, based on the thickness of the object, an irradiation condition, the irradiation condition being information related to an X-ray radiation amount of the X-ray source; and outputting the irradiation condition.

According to a further aspect of an exemplary embodiment, a non-transitory computer-readable recording medium has recorded thereon a program, which, when executed by a computer, performs the method.

BRIEF DESCRIPTION OF THE DRAWINGS

These and other aspects will become apparent and more readily appreciated from the following description of the exemplary embodiments, taken in conjunction with the accompanying drawings in which:

FIG. 19 is a table of first relationship information that may be stored in a memory of the X-ray apparatus of FIG. 13, according to an exemplary embodiment;

FIG. 20 is a table of second relationship information that may be stored in a memory of the X-ray apparatus of FIG. 13, according to an exemplary embodiment;

DETAILED DESCRIPTION

Figure 1:
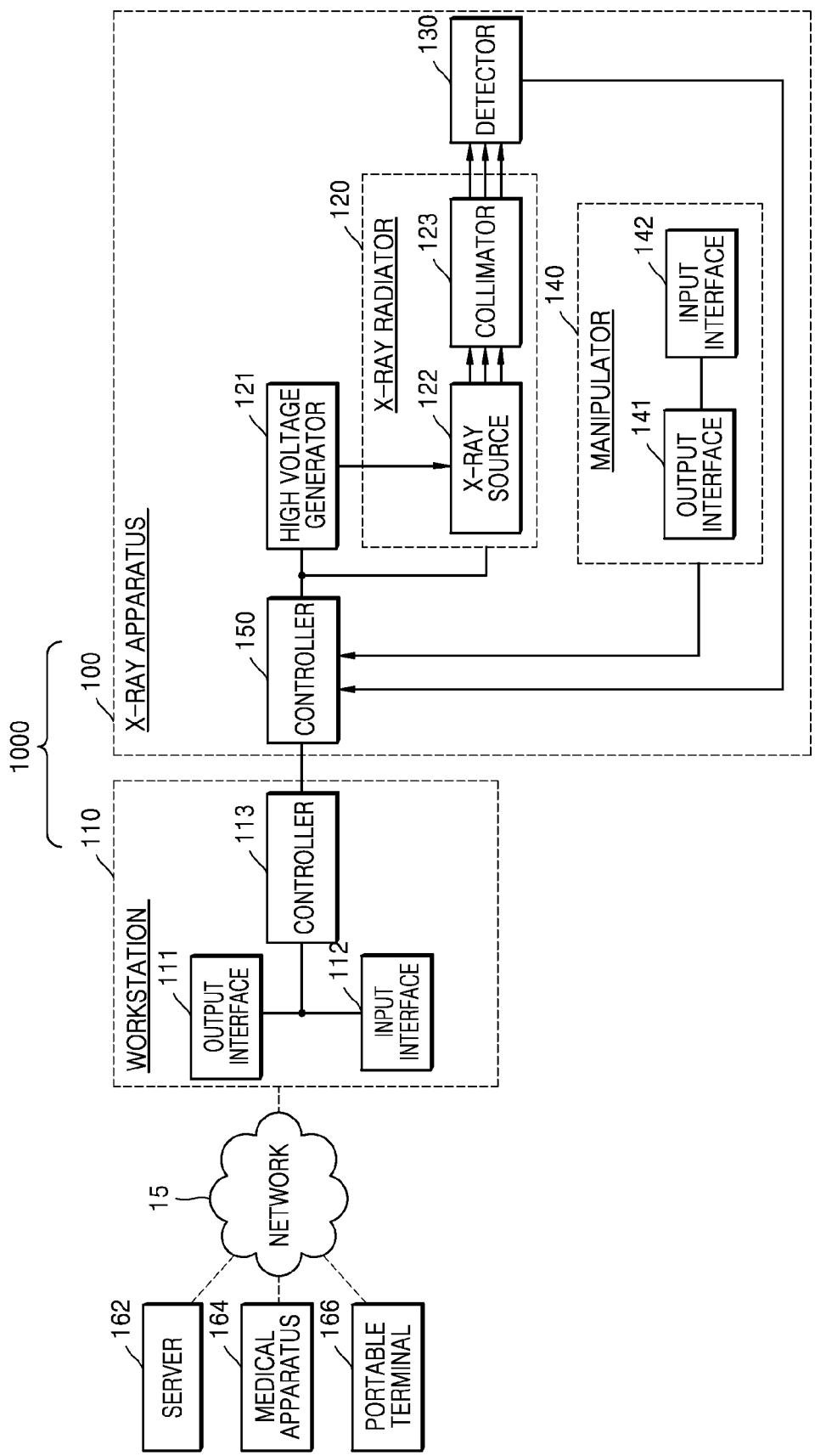
FIG. 1 is a block diagram of an X-ray system, according to an exemplary embodiment.

The attached drawings for illustrating exemplary embodiments of the present disclosure are referred to in order to gain a sufficient understanding of the present disclosure, the merits thereof, and the objectives accomplished by the implementation of the present disclosure. The present disclosure may, however, be embodied in many different forms and should not be construed as being limited to the exemplary embodiments set forth herein; rather, these exemplary embodiments are provided such that this disclosure will be thorough and complete, and will fully convey concepts to one of ordinary skill in the art. As used herein, the term "and/or" includes any and all combinations of one or more of the associated listed items. Expressions such as "at least one of," when preceding a list of elements, modify the entire list of elements and do not modify the individual elements of the list.

Hereinafter, the terms used in the specification will be briefly described, and then the present disclosure will be described in detail.

The terms used in this specification are those general terms currently widely used in the art in consideration of functions regarding the present disclosure, but the terms may vary according to the intention of those of ordinary skill in the art, precedents, or new technology in the art. Also, specified terms may be selected by the applicant, and in this case, the detailed meaning thereof will be described in the detailed description. Thus, the terms used in the specification should be understood not as simple names but based on the meaning of the terms and the overall description.

Throughout the specification, an "image" may denote multi-dimensional data composed of discrete image elements (for example, pixels in a two-dimensional image and voxels in a three-dimensional image). For example, an image may be a medical image of an object acquired by an X-ray apparatus, a computed tomography (CT) apparatus, a magnetic resonance imaging (MRI) apparatus, an ultrasound diagnosis apparatus, or another medical imaging apparatus.

In addition, an "object" may be a human, an animal, or a part of a human or animal. For example, the object may include an organ (for example, the liver, the heart, the womb, the brain, breasts, or the abdomen), blood vessels, or a combination thereof. The object may be a phantom. The term "phantom" may denote a material having a volume, a density, and an effective atomic number that are approximately the same as those of a living organism. For example, the phantom may be a spherical phantom having similar properties to those of the human body.

Throughout the specification, a "user" may be, but is not limited to, a medical expert, for example, a medical doctor, a nurse, a medical laboratory technologist, or a medical imaging expert, or a technician who repairs medical apparatuses.

An X-ray apparatus may be a medical imaging apparatus that acquires images of internal structures of an object by transmitting an X-ray through the human body. The X-ray apparatus may acquire medical images of an object more simply within a shorter time than other medical imaging apparatuses including an MRI apparatus and a CT apparatus. Therefore, the X-ray apparatus is widely used in simple chest imaging, simple abdomen imaging, simple skeleton imaging, simple nasal sinuses imaging, simple neck soft tissue imaging, and breast imaging, among other imaging situations.

FIG. 1 is a block diagram of an exemplary embodiment of an X-ray system 1000. Referring to FIG. 1, the example X-ray system 1000 includes an X-ray apparatus 100 and a workstation 110. The X-ray apparatus 100 shown in FIG. 1 may be a fixed-type X-ray apparatus or a mobile X-ray apparatus. The X-ray apparatus 100 may include an X-ray radiator 120, a high voltage generator 121, a detector 130, a manipulator 140, and a controller 150. The controller 150 may control overall operations of the X-ray apparatus 100.

The high voltage generator 121 may generate a high voltage for generating X-rays, and apply the high voltage to an X-ray source 122.

The X-ray radiator 120 includes the X-ray source 122 receiving the high voltage from the high voltage generator 121 to generate and radiate X-rays, and a collimator 123 for guiding a path of the X-ray radiated from the X-ray source 122 and adjusting an X-ray irradiation region.

The X-ray source 122 includes an X-ray tube that may be a vacuum tube diode including a cathode and an anode. An inside of the X-ray tube is set as a high vacuum state of about 10 mmHg, and a filament of the anode is heated to a high temperature to generate thermal electrons. The filament may be a tungsten filament, and a voltage of about 10V and a current of about 3 to 5 A may be applied to an electric wire connected to the filament to heat the filament.

In addition, when a high voltage of, for example, about 10 to about 300 kVp is applied between the cathode and the anode, the thermal electrons are accelerated to collide with a target material of the cathode, and then, an X-ray is generated. The X-ray is radiated outside via a window, and the window may be formed of a beryllium thin film. In this case, most of the energy of the electrons colliding with the target material may be consumed as heat, and remaining energy converted into the X-ray.

The cathode may be mainly formed of copper, and the target material may be disposed opposite to the anode. The target material may be a high resistive material such as chromium (Cr), iron (Fe), cobalt (Co), nickel (Ni), tungsten (W), or molybdenum (Mo). The target material may be rotated by a rotating field. When the target material is rotated, an electron impact area is increased, and a heat accumulation rate per unit area may be increased to be at least ten times greater than that of a case where the target material is fixed.

The voltage applied between the cathode and the anode of the X-ray tube may be referred to as a tube voltage, and the tube voltage is applied from the high voltage generator 121 and a magnitude of the tube voltage may be expressed by a crest value (kVp). When the tube voltage increases, a velocity of the thermal electrons increases, and accordingly, an energy of the X-ray (energy of photon) that is generated when the thermal electrons collide with the target material is increased. The current flowing in the X-ray tube may be referred to as a tube current that may be expressed as an average value (mA). When the tube current increases, the number of thermal electrons emitted from the filament is increased, and accordingly, the X-ray dose (the number of X-ray photons) generated when the thermal electrons collide with the target material is increased.

Therefore, the energy of the X-ray may be adjusted according to the tube voltage, and the intensity of the X-ray or the X-ray dose may be adjusted according to the tube current and the X-ray exposure time.

The detector 130 detects an X-ray that is radiated from the X-ray radiator 120 and has been transmitted through an object. The detector 130 may be a digital detector. The detector 130 may be implemented by using a thin film transistor (TFT) or a charge coupled device (CCD). Although the detector 130 is included in the X-ray apparatus 100 in FIG. 1, the detector 130 may be an X-ray detector that is a separate device capable of being connected to or separated from the X-ray apparatus 100.

The X-ray apparatus 100 may further include a manipulator 140 for providing a user with an interface for manipulating the X-ray apparatus 100. The manipulator 140 may include an output interface 141 and an input interface 142. The input interface 142 may receive from a user a command for manipulating the X-ray apparatus 100 and various types of information related to X-ray imaging. The controller 150 may control or manipulate the X-ray apparatus 100 according to the information received by the input interface 142. The output interface 141 may, for example, output sound representing information related to an imaging operation such as the X-ray radiation under the control of the controller 150.

The workstation 110 and the X-ray apparatus 100 may be connected to each other by wire or wirelessly. When they are connected to each other wirelessly, a device for synchronizing clock signals with each other may be further included. The workstation 110 and the X-ray apparatus 100 may exist within physically separate spaces.

The workstation 110 may include an output interface 111, an input interface 112, and a controller 113. The output interface 111 and the input interface 112 provide a user with an interface for manipulating the workstation 110 and the X-ray apparatus 200. The controller 113 may control the workstation 110 and the X-ray apparatus 200.

The X-ray apparatus 100 may be controlled via the workstation 110 or may be controlled by the controller 150 included in the X-ray apparatus 100. Accordingly, a user may control the X-ray apparatus 100 via the workstation 110 or may control the X-ray apparatus 100 via the manipulator 140 and the controller 150 included in the X-ray apparatus 100. In other words, a user may remotely control the X-ray apparatus 100 via the workstation 110 or may directly control the X-ray apparatus 100.

Although the controller 113 of the workstation 110 is separate from the controller 150 of the X-ray apparatus 100 in FIG. 1, FIG. 1 is only an example. As another example, the controllers 113 and 150 may be integrated into a single controller, and the single controller may be included in only one of the workstation 110 and the X-ray apparatus 100. Hereinafter, the controllers 113 and 150 may denote at least one from among the controller 113 of the workstation 110 and the controller 150 of the X-ray apparatus 100.

The output interface 111 and the input interface 112 of the workstation 110 may provide a user with an interface for manipulating the X-ray apparatus 100, and the output interface 141 and the input interface 142 of the X-ray apparatus 100 may also provide a user with an interface for manipulating the X-ray apparatus 100. Although the workstation 110 and the X-ray radiation apparatus 100 include the output interfaces 111 and 141, respectively, and the input interfaces 112 and 142, respectively, in FIG. 1, exemplary embodiments are not limited thereto. Only one of the workstation 110 and the X-ray apparatus 100 may include an output interface or an input interface.

Hereinafter, the input interfaces 112 and 142 may denote at least one from among the input interface 112 of the workstation 110 and the input interface 142 of the X-ray apparatus 100, and the output interfaces 111 and 141 may denote at least one from among the output interface 111 of the workstation 110 and the output interface 141 of the X-ray apparatus 100.

Examples of the input interfaces 112 and 142 may include a keyboard, a mouse, a touch screen, a voice recognizer, a fingerprint recognizer, an iris recognizer, and other input devices which are well known to one of ordinary skill in the art. The user may input a command for radiating the X-ray via the input interfaces 112 and 142, and the input interfaces 112 and 142 may include a switch for inputting the command. In some exemplary embodiments, the switch may be configured so that a radiation command for radiating the X-ray may be input only when the switch is pushed twice.

In other words, when the user pushes the switch, a prepare command for performing a pre-heating operation for X-ray radiation may be input through the switch, and then, when the user pushes the switch once more, the radiation command for performing substantial X-ray radiation may be input through the switch. When the user manipulates the switch as described above, the controllers 113 and 150 generate signals corresponding to the commands input through the switch manipulation, that is, for example, a prepare signal, and transmit the generated signals to the high voltage generator 121 generating a high voltage for generating the X-ray.

When the high voltage generator 121 receives the prepare signal from the controllers 113 and 150, the high voltage generator 121 starts a pre-heating operation, and when the pre-heating is finished, the high voltage generator 121 outputs a ready signal to the controllers 113 and 150. In addition, the detector 130 also needs to prepare to detect the X-ray, and thus the high voltage generator 121 performs the pre-heating operation and the controllers 113 and 150 transmit a prepare signal to the detector 130 so that the detector 130 may prepare to detect the X-ray transmitted through the object. The detector 130 prepares to detect the X-ray in response to the prepare signal, and when the preparing for the detection is finished, the detector 130 outputs a ready signal to the controllers 113 and 150.

When the pre-heating operation of the high voltage generator 121 is finished and the detector 130 is ready to detect the X-ray, the controllers 113 and 150 transmit a radiation signal to the high voltage generator 121, the high voltage generator 121 generates and applies the high voltage to the X-ray source 122, and the X-ray source 122 radiates the X-ray.

When the controllers 113 and 150 transmit the radiation signal to the high voltage generator 121, the controllers 113 and 150 may transmit a sound output signal to the output interfaces 111 and 141 so that the output interfaces 111 and 141 output a predetermined sound and the object may recognize the radiation of the X-ray. The output interfaces 111 and 141 may also output a sound representing information related to imaging in addition to the X-ray radiation. In FIG. 1, the output interface 141 is included in the manipulator 140; however, the exemplary embodiments are not limited thereto, and the output interface 141 or a portion of the output interface 141 may be located elsewhere. For example, the output interface 141 may be located on a wall of an examination room in which the X-ray imaging of the object is performed.

The controllers 113 and 150 control locations of the X-ray radiator 120 and the detector 130, imaging timing, and imaging conditions, according to imaging conditions set by the user.

In more detail, the controllers 113 and 150 control the high voltage generator 121 and the detector 130 according to the command input via the input interfaces 112 and 142 in order to control radiation timing of the X-ray, an intensity of the X-ray, and a region radiated by the X-ray. In addition, the control units 113 and 150 adjust the location of the detector 130 according to a predetermined imaging condition, and controls operation timing of the detector 130.

Furthermore, the controllers 113 and 150 generate a medical image of the object by using image data received via the detector 130. In detail, the controllers 113 and 150 may receive the image data from the detector 130, and then, generate the medical image of the object by removing noise from the image data and adjusting a dynamic range and interleaving of the image data.

The output interfaces 111 and 141 may output the medical image generated by the controllers 113 and 150. The output interfaces 111 and 141 may output information that is necessary for the user to manipulate the X-ray apparatus 100, for example, a user interface (UI), user information, or object information. Examples of the output interfaces 111 and 141 may include a speaker, a printer, a cathode ray tube (CRT) display, a liquid crystal display (LCD), a plasma display panel (PDP), an organic light emitting diode (OLED) display, a field emission display (FED), a light emitting diode (LED) display, a vacuum fluorescent display (VFD), a digital light processing (DLP) display, a flat panel display (FPD), a three-dimensional (3D) display, a transparent display, and other various output devices well known to one of ordinary skill in the art.

The workstation 110 shown in FIG. 1 may further include a communicator that may be connected to a server 162, a medical apparatus 164, and a portable terminal 166 via a network 15.

The communicator may be connected to the network 15 by wire or wirelessly to communicate with the server 162, the medical apparatus 164, or the portable terminal 166. The communicator may transmit or receive data related to diagnosis of the object via the network 15, and may also transmit or receive medical images captured by the medical apparatus 164, for example, a CT apparatus, an MRI apparatus, or an X-ray apparatus. Moreover, the communicator may receive a medical history or treatment schedule of an object (e.g., a patient) from the server 162 to diagnose a disease of the object. Also, the communicator may perform data communication with the portable terminal 166 such as a mobile phone, a personal digital assistant (PDA), or a laptop computer of a medical doctor or a client, as well as the server 162 or the medical apparatus 164 in a hospital.

The communicator may include one or more elements enabling communication with external apparatuses. For example, the communicator may include a local area communication module, a wired communication module, and a wireless communication module.

The local area communication module may refer to a module for performing local area communication with an apparatus located within a predetermined distance. Examples of local area communication technology may include, but are not limited to, a wireless local area network (LAN), Wi-Fi, Bluetooth, ZigBee, Wi-Fi Direct (WFD), ultra wideband (UWD), infrared data association (IrDA), Bluetooth low energy (BLE), and near field communication (NFC).

The wired communication module may refer to a module for communicating by using an electric signal or an optical signal. Examples of wired communication technology may include wired communication techniques using a pair cable, a coaxial cable, and an optical fiber cable, and other wired communication techniques that are well known to one of ordinary skill in the art.

The wireless communication module transmits and receives a wireless signal to and from at least one selected from a base station, an external apparatus, and a server in a mobile communication network. Here, examples of the wireless signal may include a voice call signal, a video call signal, and various types of data according to text/multimedia messages transmission.

The X-ray apparatus 100 shown in FIG. 1 may include a plurality of digital signal processors (DSPs), an ultra-small calculator, and a processing circuit for special purposes (for example, high speed analog/digital (A/D) conversion, high speed Fourier transformation, and an array process).

In addition, communication between the workstation 110 and the X-ray apparatus 100 may be performed using a high speed digital interface, such as low voltage differential signaling (LVDS), asynchronous serial communication, such as a universal asynchronous receiver transmitter (UART), a low latency network protocol, such as error synchronous serial communication or a controller area network (CAN), or any of other various communication methods that are well known to one of ordinary skill in the art.

Figure 2:
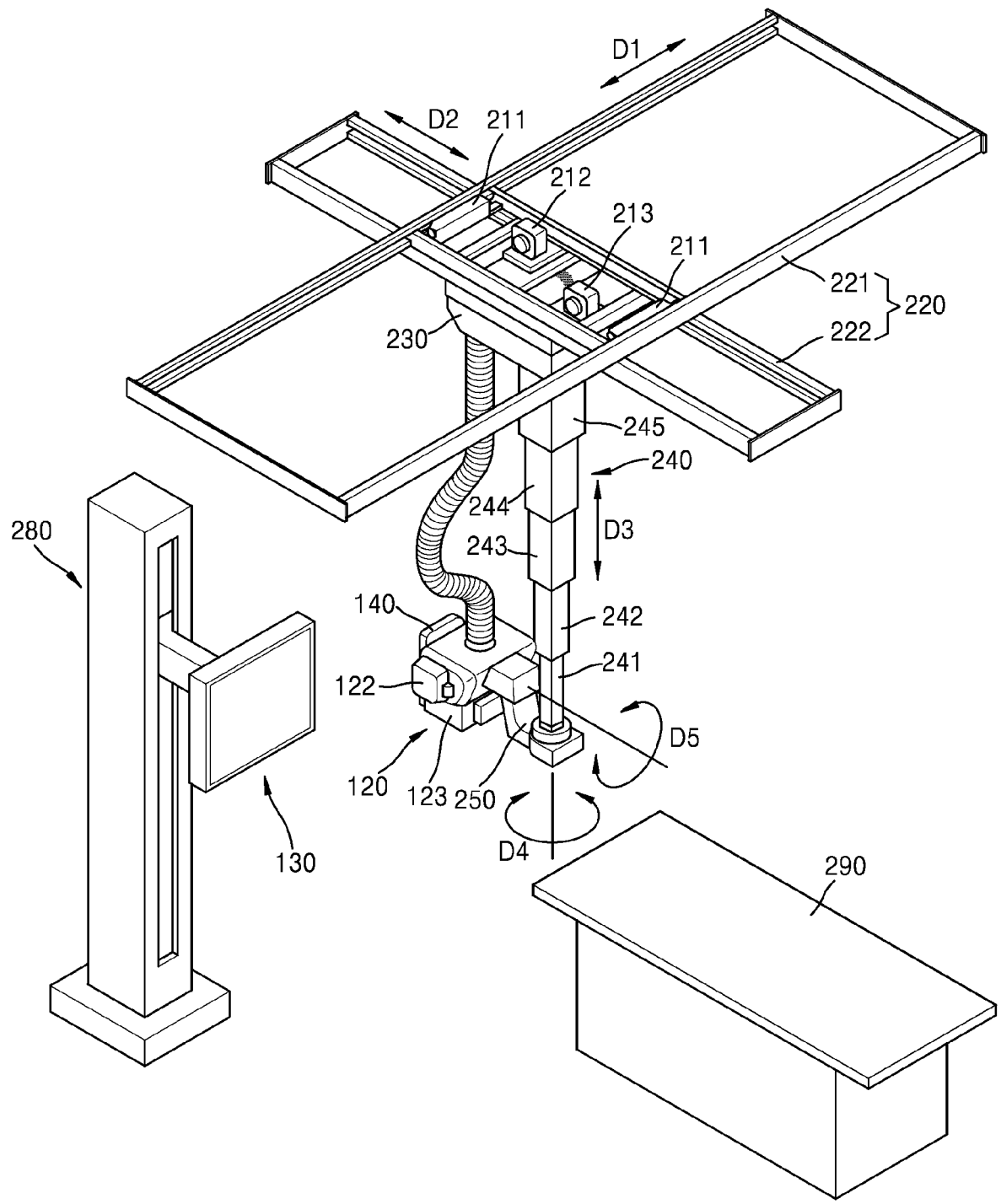
FIG. 2 is a perspective view of a fixed type X-ray apparatus, according to an exemplary embodiment.

FIG. 2 is a perspective view of an example of a fixed type X-ray apparatus 200 according to an exemplary embodiment. The fixed type X-ray apparatus 200 may be another exemplary embodiment of the X-ray apparatus 100 of FIG. 1. Components included in the fixed type X-ray apparatus 200 that are the same as those of the X-ray apparatus 100 of FIG. 1 use the same reference numerals, and repeated descriptions thereof will be omitted.

Referring to FIG. 2, the example fixed type X-ray apparatus 200 includes a manipulator 140 providing a user with an interface for manipulating the X-ray apparatus 200, an X-ray radiator 120 radiating an X-ray to an object, a detector 130 detecting an X-ray that has passed through the object, first, second, and third motors 211, 212, and 213 providing a driving power to transport the X-ray radiator 120, a guide rail 220, a moving carriage 230, and a post frame 240. The guide rail 220, the moving carriage 230, and the post frame 240 are formed to transport the X-ray radiator 120 by using the driving power of the first, second, and third motors 211, 212, and 213.

The guide rail 220 includes a first guide rail 221 and a second guide rail 222 that are provided to form a predetermined angle with respect to each other. The first guide rail 221 and the second guide rail 222 may respectively extend in directions crossing each other at 90°.

The first guide rail 221 is provided on the ceiling of an examination room in which the X-ray apparatus 200 is disposed.

The second guide rail 222 is located under the first guide rail 221, and is mounted so as to slide along the first guide rail 221. A roller that may move along the first guide rail 221 may be provided on the first guide rail 221. The second guide rail 222 is connected to the roller to move along the first guide rail 221.

A first direction D1 is defined as a direction in which the first guide rail 221 extends, and a second direction D2 is defined as a direction in which the second guide rail 222 extends. Therefore, the first direction D1 and the second direction D2 cross each other at 90°, and may be parallel to the ceiling of the examination room.

The moving carriage 230 is disposed under the second guide rail 222 so as to move along the second guide rail 222. A roller moving along the second guide rail 222 may be provided on the moving carriage 230.

Therefore, the moving carriage 230 may move in the first direction D1 together with the second guide rail 222, and may move in the second direction D2 along the second guide rail 222.

The post frame 240 is fixed on the moving carriage 230 and located under the moving carriage 230. The post frame 240 may include a plurality of posts 241, 242, 243, 244, and 245.

In some exemplary embodiments, the plurality of posts 241, 242, 243, 244, and 245 are connected to each other to be foldable, nestable, or retractable within each other, and thus, the post frame 240 may have a length that is adjustable in a vertical direction of the examination room while in a state of being fixed to the moving carriage 230.

A third direction D3 is defined as a direction in which the length of the post frame 240 increases or decreases. Therefore, the third direction D3 may be perpendicular to the first direction D1 and the second direction D2.

The detector 130 detects the X-ray that has passed through the object, and may be combined with a table type receptor 290 or a stand type receptor 280.

A rotating joint 250 is disposed between the X-ray radiator 120 and the post frame 240. The rotating joint 250 allows the X-ray radiator 120 to be coupled to the post frame 240, and supports a load applied to the X-ray radiator 120.

The X-ray radiator 120 connected to the rotating joint 250 may rotate on a plane that is perpendicular to the third direction D3. In this case, a rotating direction of the X-ray radiator 120 may be defined as a fourth direction D4.

Also, the X-ray radiator 120 may be configured to be rotatable on a plane perpendicular to the ceiling of the examination room. Therefore, the X-ray radiator 120 may rotate in a fifth direction D5 that is a rotating direction about an axis that is parallel with the first direction D1 or the second direction D2, with respect to the rotating joint 250.

The first, second, and third motors 211, 212, and 213 may be provided to move the X-ray radiator 120 in the first, second, and third directions D1, D2, and D3. The first, second, and third motors 211, 212, and 213 may be electrically driven, and the first, second, and third motors 211, 212, and 213 may respectively include an encoder.

The first, second, and third motors 211, 212, and 213 may be disposed at various locations in consideration of design convenience. For example, the first motor 211, moving the second guide rail 222 in the first direction D1, may be disposed around the first guide rail 221, the second motor 212, moving the moving carriage 230 in the second direction D2, may be disposed around the second guide rail 222, and the third motor 213, increasing or reducing the length of the post frame 240 in the third direction D3, may be disposed in the moving carriage 230. In another example, the first, second, and third motors 211, 212, and 213 may be connected to a power transfer unit in order to linearly move the X-ray radiator 120 in the first, second, and third directions D1, D2, and D3. The driving power transfer unit may be a combination of a belt and a pulley, a combination of a chain and a sprocket, or a shaft, which are generally used.

In another example, motors may be disposed between the rotating joint 250 and the post frame 240 and between the rotating joint 250 and the X-ray radiator 120 in order to rotate the X-ray radiator 120 in the fourth and fifth directions D4 and D5.

The manipulator 140 may be disposed on a side surface of the X-ray radiator 120.

Although FIG. 2 shows the fixed type X-ray apparatus 200 connected to the ceiling of the examination room, the fixed type X-ray apparatus 200 is merely an example for convenience of comprehension. That is, X-ray apparatuses according to exemplary embodiments of the present disclosure may include X-ray apparatuses having various structures that are well known to one of ordinary skill in the art, for example, a C-arm-type X-ray apparatus and an angiography X-ray apparatus, in addition to the fixed type X-ray apparatus 200 of FIG. 2.

Figure 3:
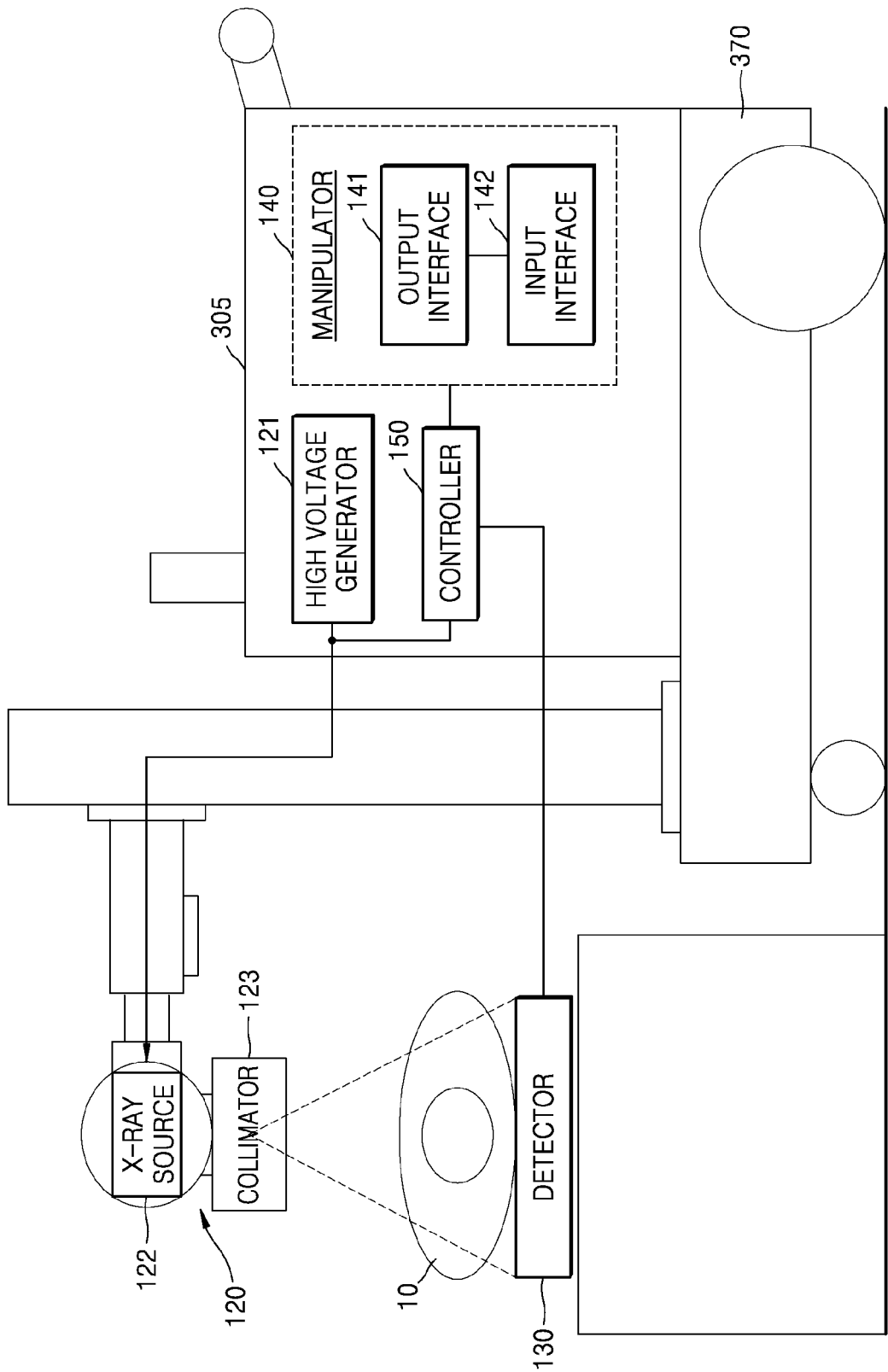
FIG. 3 is a diagram showing a configuration of a mobile X-ray apparatus, according to an exemplary embodiment.

FIG. 3 is a diagram showing an example configuration of a mobile X-ray apparatus 300 capable of performing an X-ray imaging operation regardless of a place where the imaging operation is performed, according to an exemplary embodiment. The mobile X-ray apparatus 300 may be another exemplary embodiment of the X-ray apparatus 100 of FIG. 1. Components included in the mobile X-ray apparatus 300 that are the same as those of the X-ray apparatus 100 of FIG. 1 use the same reference numerals as those used in FIG. 1, and a repeated description thereof will be omitted.

Referring to FIG. 3, the example mobile X-ray apparatus 300 includes a transport unit 370 including a wheel for transporting the mobile X-ray apparatus 300, a main unit 305, an X-ray radiator 120, and a detector 130 detecting an X-ray that is radiated from the X-ray radiator 120 toward an object and transmitted through the object. The main unit 305 includes a manipulator 140 providing a user with an interface for manipulating the mobile X-ray apparatus 300, a high voltage generator 121 generating a high voltage applied to an X-ray source 122, and a controller 150 controlling overall operations of the mobile X-ray apparatus 300. The X-ray radiator 120 includes the X-ray source 122 generating the X-ray, and a collimator 123 guiding a path along which the generated X-ray is emitted from the X-ray source 122 and adjusting an irradiation region radiated by the X-ray.

The detector 130 in FIG. 3 may be not combined with any receptor, and the detector 130 may be a portable detector which can exist anywhere.

In FIG. 3, the manipulator 140 is included in the main unit 305; however, exemplary embodiments are not limited thereto. For example, as illustrated in FIG. 2, the manipulator 140 of the mobile X-ray apparatus 300 may be disposed on a side surface of the X-ray radiator 120.

The controller 150 controls locations of the X-ray radiator 120 and the detector 130, imaging timing, and imaging conditions according to imaging conditions set by the user.

In addition, the controller 150 generates a medical image of the object by using image data received from the detector 130. In detail, the controller 150 may generate the medical image of the object by removing noise from the image data received from the detector 130 and adjusting a dynamic range and interleaving of the image data.

The main unit 305 of the mobile X-ray apparatus 300 shown in FIG. 3 may further include an output interface outputting the medical image generated by the controller 150. The output interface may output information that is necessary for the user to manipulate the mobile X-ray apparatus 300, for example, a UI, user information, or object information.

Figure 4:
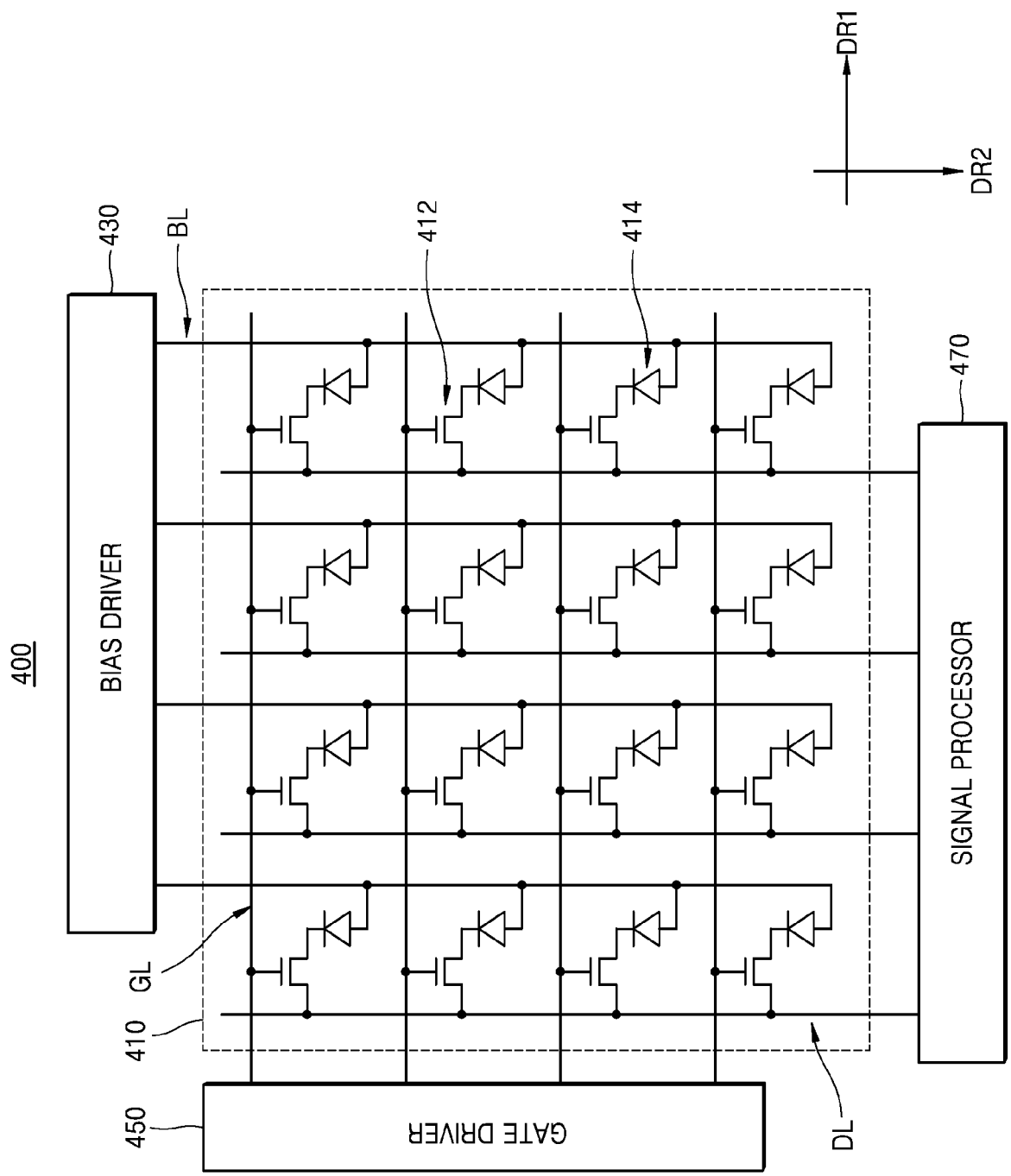
FIG. 4 is a schematic diagram showing a detailed configuration of a detector, according to an exemplary embodiment.

FIG. 4 is a schematic diagram showing an example of a detailed configuration of a detector 400, according to an exemplary embodiment. The detector 400 may be an exemplary embodiment of the detector 130 of FIGS. 1-3. The detector 400 may be an indirect type detector.

Referring to FIG. 4, the detector 400 may include a scintillator, a photodetecting substrate 410, a bias driver 430, a gate driver 450, and a signal processor 470.

The scintillator receives the X-ray radiated from the X-ray source 122 and converts the X-ray into light.

The photodetecting substrate 410 receives the light from the scintillator and converts the light into an electrical signal. The photodetecting substrate 410 may include gate lines GL, data lines DL, TFTs 412, photodiodes 414, and bias lines BL.

The gate lines GL may be formed in a first direction DR1, and the data lines DL may be formed in a second direction DR2 that crosses the first direction DR1. The first direction DR1 and the second direction DR2 may intersect perpendicularly to each other. FIG. 4 shows four gate lines GL and four data lines DL as an example.

The TFTs 412 may be arranged as a matrix in the first and second directions DR1 and DR2. Each of the TFTs 412 may be electrically connected to one of the gate lines GL and one of the data lines DL. A gate of the TFT 412 may be electrically connected to the gate line GL, and a source of the TFT 412 may be electrically connected to the data line DL. In FIG. 4, sixteen TFTs 412 (in a 4×4 arrangement) are shown as an example.

The photodiodes 414 may be arranged as a matrix in the first and second directions DR1 and DR2 so as to respectively correspond to the TFTs 412. Each of the photodiodes 414 may be electrically connected to one of the TFTs 412. An N-side electrode of each of the photodiodes 414 may be electrically connected to a drain of the TFT 412. FIG. 4 shows sixteen photodiodes 414 (in a 4×4 arrangement) as an example.

The bias lines BL are electrically connected to the photodiodes 414. Each of the bias lines BL may be electrically connected to P-side electrodes of an array of photodiodes 414. For example, the bias lines BL may be formed to be substantially parallel with the second direction DR2 so as to be electrically connected to the photodiodes 414. On the other hand, the bias lines BL may be formed to be substantially parallel with the first direction DR1 in order to be electrically connected to the photodiodes 414. FIG. 4 shows four bias lines BL formed along the second direction DR2 as an example.

The bias driver 430 is electrically connected to the bias lines BL in order to apply a driving voltage to the bias lines BL. The bias driver 430 may selectively apply a reverse bias voltage or a forward bias voltage to the photodiodes 414. A reference voltage may be applied to the N-side electrodes of the photodiodes 414. The reference voltage may be applied via the signal processor 470. The bias driver 430 may apply a voltage that is less than the reference voltage to the P-side electrodes of the photodiodes 414 in order to apply a reverse bias voltage to the photodiodes 414. On the other hand, the bias driver 430 may apply a voltage that is greater than the reference voltage to the P-side electrodes of the photodiodes 414 so as to apply a forward bias voltage to the photodiodes 414.

The gate driver 450 is electrically connected to the gate lines GL and thus may apply gate signals to the gate lines GL. For example, when the gate signals are applied to the gate lines GL, the TFTs 412 may be turned on by the gate signals. On the other hand, when the gate signals are not applied to the gate lines GL, the TFTs 412 may be turned off.

The signal processor 470 is electrically connected to the data lines DL. When the light received by the photodetecting substrate 410 is converted into the electrical signal, the electrical signal may be read out by the signal processor 470 via the data lines DL.

An operation of the detector 400 will now be described. During the operation of the detector 400, the bias driver 430 may apply the reverse bias voltage to the photodiodes 414.

While the TFTs 412 are turned off, each of the photodiodes 414 may receive the light from the scintillator and generate electron-hole pairs to accumulate electric charges. The amount of electric charge accumulated in each of the photodiodes 414 may correspond to the intensity of the received X-ray.

Then, the gate driver 450 may sequentially apply the gate signals to the gate lines GL along the second direction DR2. When a gate signal is applied to a gate line GL and thus TFTs 412 connected to the gate line GL are turned on, photocurrents may flow into the signal processor 470 via the data lines DL due to the electric charges accumulated in the photodiodes 414 connected to the turned-on TFTs 412.

The signal processor 470 may convert the received photocurrents into image data and output the image data to the outside. The image data may be in the form of an analog signal or a digital signal corresponding to the photocurrents.

Although not shown in FIG. 4, if the detector 400 shown in FIG. 4 is a wireless detector, the detector 400 may further include a battery unit and a wireless communication interface unit.

Figure 5:
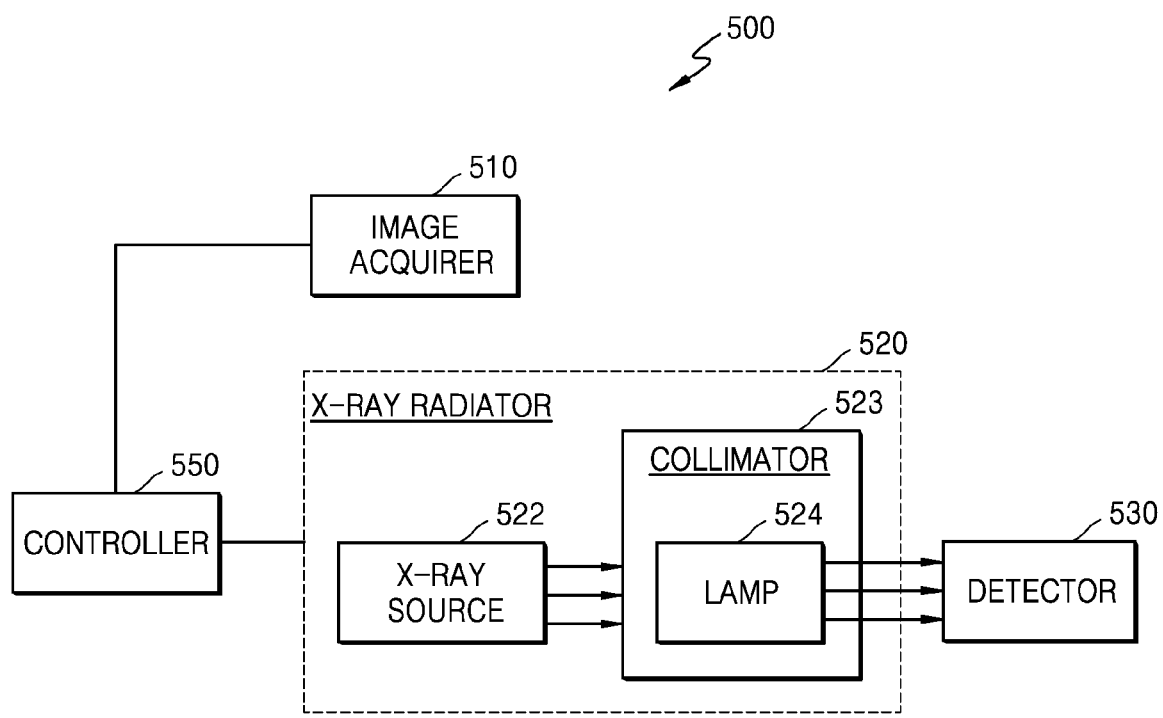
FIG. 5 is a block diagram of an X-ray apparatus according to an exemplary embodiment.

FIG. 5 is a block diagram of an example of an X-ray apparatus 500 according to an exemplary embodiment. The X-ray apparatus 500 of FIG. 5 may be another exemplary embodiment of the above-described X-ray apparatuses 100, 200, and 300. Therefore, whether or not described below, the above-described features may be applied to the X-ray apparatus 500 of FIG. 5. Also, the X-ray apparatus 500 may be controlled by the workstation 110 of FIG. 1.

Referring to FIG. 5, the X-ray apparatus 500 may include an image acquirer 510, an X-ray radiator 520, a detector 530, and a controller 550. The X-ray radiator 520 includes an X-ray source 522 and a collimator 523.

The X-ray source 522 may radiate X-rays. The collimator 523 may adjust an irradiation region of X-rays radiated by the X-ray source 522. The detector 530 detects X-rays. Hereinafter in the present specification, a detector may also be referred to as an "X-ray detector." Also, because an X-ray image is acquired based on X-rays detected by the detector 530, the detector 530 may also be referred to as an image receptor. Although FIG. 5 illustrates that the detector 530 is included in the X-ray apparatus 500, the detector 530 may be an X-ray detector that may be connected to or separated from the X-ray apparatus 500.

The collimator 523 includes a lamp 524. The lamp 524 may be turned on and off. The lamp 524 may include various types of light emission sources. When the lamp 524 is turned on, light is emitted from the lamp 524.

The image acquirer 510 may acquire an image of an object by imaging an object while the lamp 524 is turned on. Hereinafter, the image acquired by imaging the object is referred to as "object image." The object image is captured via imaging, and is different from an X-ray image that is acquired by capturing an object using X-rays. The image acquirer 510 may include various types of imaging devices, such as a camera or a camcorder.

The controller 550 may include a central processing unit (CPU), a microprocessor, a graphic processing unit (GPU), and the like.

The controller 550 may acquire a distance between the X-ray source 522 and the object based on the object image acquired by the image acquirer 510. Hereinafter, a distance between an X-ray source and an object is referred to as "object distance" or "source to object distance (SOD)."

The controller 550 may detect a certain area or a certain point in an object image. According to a relationship between a region and the SOD or a relationship between a point and the SOD, the controller 550 may acquire the SOD based on a detected region or a detected point. A method of acquiring an object distance based on an object image will be described below with reference to the following drawings.

The controller 550 may acquire a thickness of the object based on the object distance, and a detector distance that is a distance between the X-ray source 522 and the detector 530. Hereinafter, a distance between an X-ray source and a detector is also referred to as "detector distance" or "source to image receptor distance SID."

Figure 6:
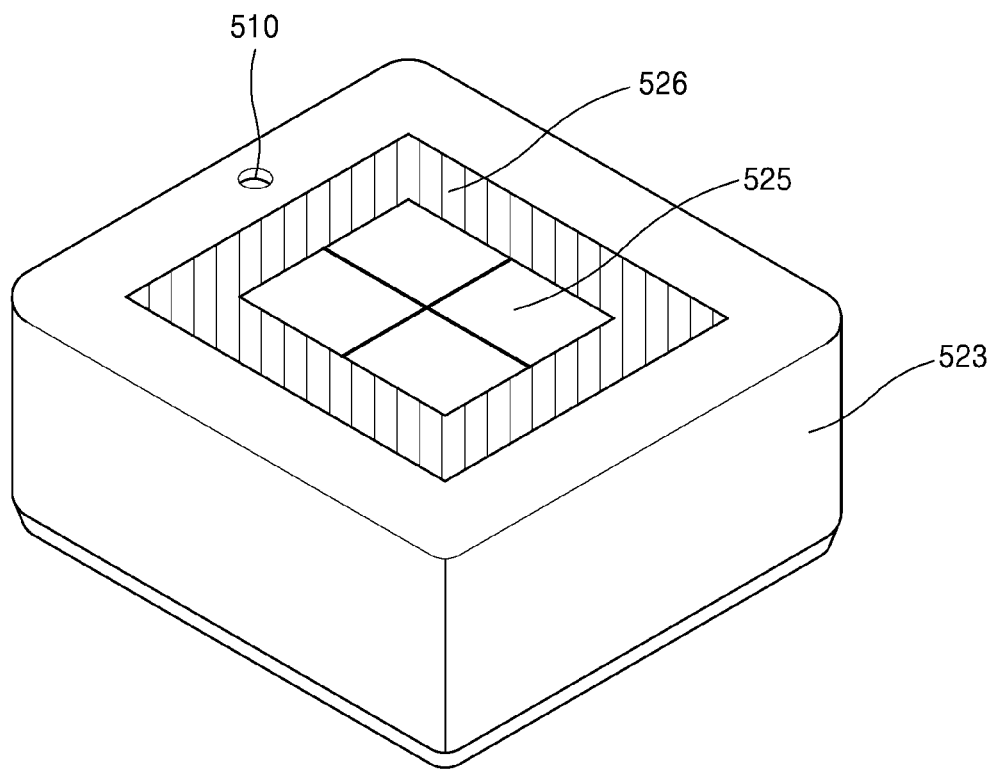
FIG. 6 is a perspective view of a collimator included in the X-ray apparatus of FIG. 5, according to an exemplary embodiment.

FIG. 6 is a perspective view of an example of the collimator 523 included in the X-ray apparatus 500 of FIG. 5, according to an exemplary embodiment.

Referring to FIGS. 5 and 6, the collimator 523 may further include an irradiation window 525 and a shutter 526.

Although not illustrated in FIG. 6, the collimator 523 may include the lamp 524 of FIG. 5.

X-rays may be radiated from the X-ray source 522 through the irradiation window 525 of the collimator 523. Also, when the lamp 524 of the collimator 523 is turned on, light is emitted through the irradiation window 525 of the collimator 523. That is, light from the lamp 524 or X-rays from the X-ray source 522 may pass through the irradiation window 525. Referring to FIG. 6, the irradiation window 525 is a quadrilateral with crossing lines. However, FIG. 6 is only an exemplary diagram of the irradiation window 525, and a shape of the irradiation window 525 is not limited to that shown in FIG. 6.

The shutter 526 may adjust a size of the irradiation window 525. The collimator 523 may adjust the size of the irradiation window 525 by using the shutter 526 to thus adjust an X-ray irradiation region.

Because light from the lamp 524 and X-rays from the X-ray source 522 are emitted through the irradiation window 525, an irradiation region of light from the lamp 524 may correspond to the X-ray irradiation region. Therefore, before the X-ray source 522 radiates X-rays, a user may recognize or adjust the X-ray irradiation region via the irradiation region of light from the lamp 524.

As shown in FIG. 6, the image acquirer 510 may be coupled to the collimator 523. However, FIG. 6 is only an exemplary diagram, and a location of the image acquirer 510 in the X-ray apparatus 500 is not limited to that shown in FIG. 6.

Figure 7:
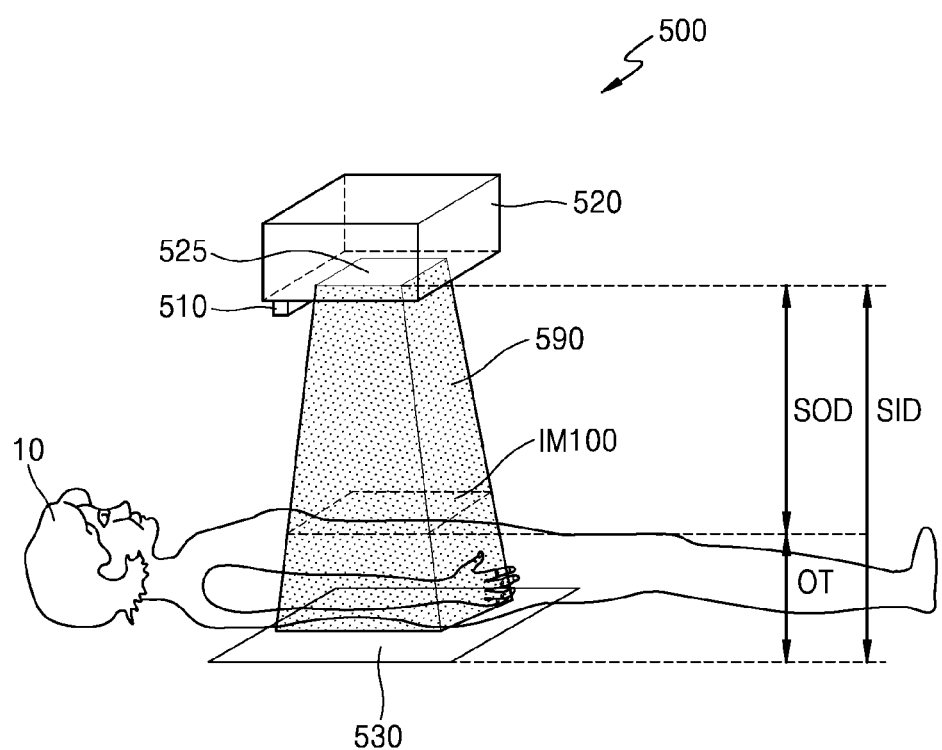
FIG. 7 is a diagram showing the X-ray apparatus of FIG. 5 according to an exemplary embodiment.

FIG. 7 is a diagram showing an example of the X-ray apparatus 500 of FIG. 5 according to an exemplary embodiment. Whether or not described below, the X-ray apparatus 500 of FIG. 7 may also include the above-described features. Also, features of FIGS. 5 and 6 that are not shown in FIG. 7 may also be included in the X-ray apparatus 500 of FIG. 7. The X-ray apparatus 500 of FIG. 7 may include the controller 550 of FIG. 5, and the X-ray radiator 520 of FIG. 7 may include the collimator 523 including the lamp 524 and the X-ray source 522 of FIG. 5.

Referring to FIGS. 5 and 7, when the lamp 524 is turned on, light from the lamp 524 is emitted through the irradiation window 525 of the collimator 523. Due to an irradiation region 590 of light from the lamp 524, an image IM100 of the irradiation window 525 may be formed on an object 10. The image of the irradiation window 525 formed on the object 10 may also be referred to as an "irradiation window image IM100" on the object 10.

The image acquirer 510 may acquire an object image by imaging the object 10. Because the irradiation window image IM100 is formed on the object 10, the object image acquired by the image acquirer 510 may include an image area corresponding to the irradiation window image IM100.

Figure 8:
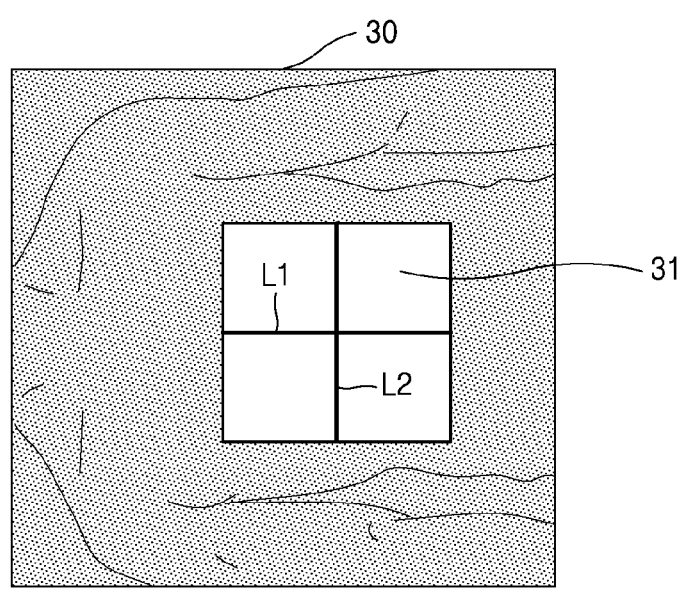
FIG. 8 is a diagram showing an object image acquired by the X-ray apparatus of FIG. 7, according to an exemplary embodiment.

FIG. 8 is a diagram showing an example of an object image 30 acquired by the X-ray apparatus 500 of FIG. 7, according to an exemplary embodiment.

Referring to FIGS. 7 and 8, the object image 30 includes an image area 31 corresponding to the irradiation window image IM100 formed on the object 10. Hereinafter, the image area 31 corresponding to the irradiation window image IM100 in the object image 30 will be referred to as "collimation region" or "irradiation region of a collimator" of the object image 30. That is, a collimation region 31 is included in the object image 30 and corresponds to the irradiation region 590 of light from the lamp 524 of the collimator 523 of FIG. 5.

The object image 30 may indicate 2-dimensional (2D) data including pixel values of pixels that are discrete image components. The pixel values may include at least one piece of information, such as brightness or color. In the object image 30, the collimation region 31 may be a group of pixels.

Referring back to FIGS. 5 to 8, the controller 550 may detect the collimation region 31 in the object image 30. The controller 550 may acquire an object distance SOD based on a size of the collimation region 31.

The controller 550 may detect the collimation region 31 based on brightness information of the object image 30. The collimation region 31 may be brighter than other areas in the object image 30. That is, pixel values of pixels in the collimation region 31 may have higher brightness than those of other areas.

Furthermore, the controller 550 may detect the collimation region 31 based on a shape of the irradiation window 525 of the collimator 523. The shape of the collimation region 31 may vary according to the shape of the irradiation window 525. For example, when the irradiation window 525 is quadrilateral-shaped as in FIG. 6, the collimation region 31 may also be quadrilateral-shaped. Also, when the irradiation window 525 has crossing lines as in FIG. 6, the collimation region 31 may also have crossing lines L1 and L2 as shown in FIG. 8. Therefore, the controller 550 may use a pattern recognition algorithm based on the shape of the irradiation window 525 to detect the collimation region 31. For example, when the irradiation window 525 is quadrilateral-shaped, the controller 550 may use a quadrilateral pattern recognition algorithm.

The controller 550 may set a predetermined error range related to the shape of the collimation region 31 that is based on the shape of the irradiation window 525 of the collimator 523. Due to curves of the object 10, the irradiation window image IM100 on the object 10 may be slightly distorted compared to an actual shape of the irradiation window 525. Accordingly, the shape of the collimation region 31 in the object image 30 may also be distorted. Therefore, the controller 550 may set a predetermined error range related to the shape of the collimation region 31. For example, when the irradiation window 525 is rectangular-shaped, the shape of the collimation region 31 may be a quadrilateral such as a trapezoid.

Also, the controller 550 may reduce the size of the irradiation window 525 by using the shutter 526 so as to reduce distortion of the shape of the collimation region 31. In this case, the collimation region 31 may also be reduced in the object image 30, and thus, the shape of the collimation region 31 may be less distorted. However, as the collimation region 31 decreases in size, accuracy of the object distance SOD acquired by the controller 550 may decrease. Therefore, the controller 550 may adjust the size of the irradiation window 525 of FIG. 6 based on trade-off with the accuracy of the object distance SOD.

Accordingly, the controller 550 may detect the collimation region 31 based on brightness information of the object image 30, the shape of the irradiation window 525, and the like. The controller 550 may acquire the object distance SOD based on the size of the collimation region 31. The size of the collimation region 31 may correspond to the number of pixels in the collimation region 31.

Alternatively, the size of the collimation region 31 may correspond to the area size of the collimation region 31. The controller 550 may detect crossing lines L1 and L2 of the object image 30 that correspond to crossing lines of the irradiation window 525, and acquire the size of the collimation region 31 based on the crossing lines L1 and L2. The controller 550 may detect the crossing lines L1 and L2 based on the brightness information of the object image 30, the shape of the irradiation window 525, and the like. The controller 550 may detect respective lengths of the crossing lines L1 and L2. For example, the respective lengths of the crossing lines L1 and L2 may correspond to the number of pixels that form each of the crossing lines L1 and L2. The controller 550 may multiply the respective lengths of the crossing lines L1 and L2 and thus acquire the size of the collimation region 31.

Alternatively, the size of the collimation region 31 may be estimated based on a length of one of the crossing lines L1 and L2. The controller 550 may acquire the size of the collimation region 31 based on a length of one of the crossing lines L1 and L2 of the irradiation window 525.

The controller 550 may acquire the object distance SOD based on the size of the collimation region 31. However, the descriptions above are only examples of a method of acquiring the size of the collimation region 31, and the method is not limited thereto.

The size of the collimation region 31 in the object image 30 may vary according to the object distance SOD. Therefore, when the controller 550 acquires relationship information that indicates relationship between the size of the collimation region 31 and the object distance SOD, the object distance SOD may be acquired based on the relationship information.

Figure 9:
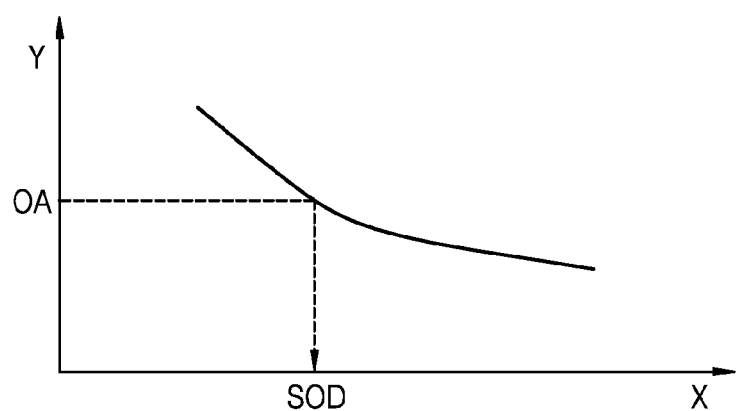
FIG. 9 is a graph of a relationship information between a size of a collimation region and an object distance, according to an exemplary embodiment.

FIG. 9 is a graph of an example of a relationship information between a size of a collimation region and an object distance, according to an exemplary embodiment.

Referring to FIG. 9, an X-axis indicates the object distance, and a Y-axis indicates a size of a collimation region in an object image. The size of the collimation decreases as the object distance increases. In perspective, the size of the collimation region in the object image may decrease as the object distance increases. Therefore, when the size (OA) of the collimation region in the object image is acquired, the object distance SOD may be acquired based on the relationship information as shown in FIG. 9.

Referring back to FIG. 7, the controller 550 of FIG. 5 may acquire the object distance SOD based on relationship information (e.g., the relationship information of FIG. 9) that indicates a relationship between the size of the collimation region and the object distance. Also, the controller 550 of FIG. 5 may acquire an object thickness OT that indicates a thickness of the object 10, based on a detector distance SID (source to image receptor distance) and an object distance SOD. The object thickness OT may be equal to a difference between the detector distance SID and the object distance SOD.

Therefore, according to an exemplary embodiment, the X-ray apparatus 500 may automatically acquire the object distance SOD, which is a distance between an X-ray source 525 and the object 10, based on an object image by imaging the object 10. Also, the X-ray apparatus 500 may acquire the object thickness OT based on the object distance SOD and the detector distance SID, which is a distance between the X-ray source 525 and the detector 530. According to an exemplary embodiment, the X-ray apparatus 500 may automatically acquire the object distance SOD or the object thickness OT without a separate sensor or a measuring instrument such as a tapeline.

Also, the controller 550 of FIG. 5 may acquire the detector distance SID in a similar manner as the acquiring of the object distance SOD. This will be described with reference to FIG. 10.

Figure 10:
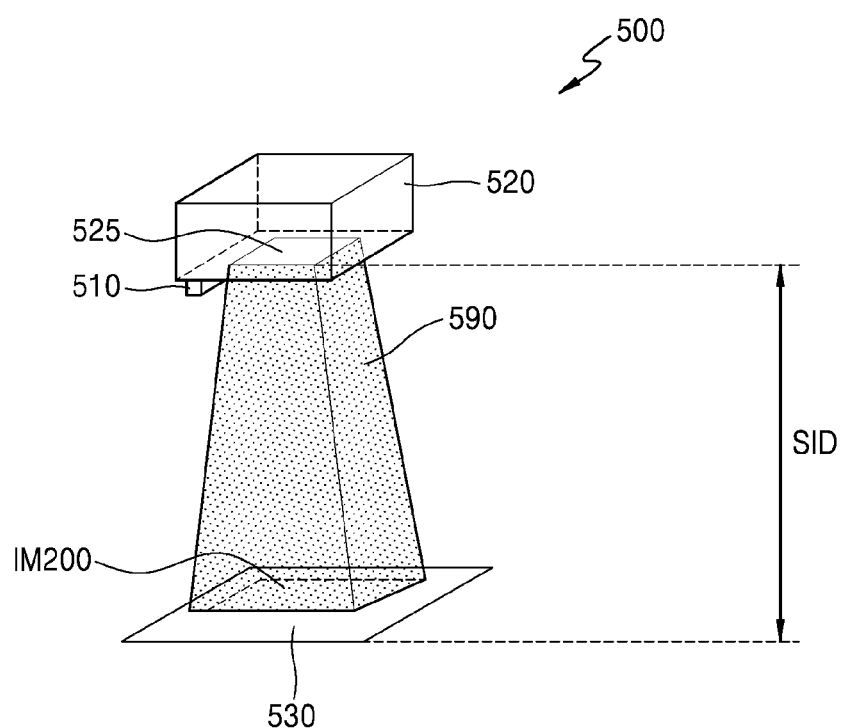
FIG. 10 is a diagram for describing acquiring a detector distance by using the X-ray apparatus of FIG. 7, according to an exemplary embodiment.

FIG. 10 is a diagram for describing an example of acquiring the detector distance SID by using the X-ray apparatus 500 of FIG. 7, according to an exemplary embodiment. The X-ray apparatus 500 of FIG. 10 may be another exemplary embodiment of the X-ray apparatus 500 of FIG. 5. The above-described features may also be applied to the X-ray apparatus 500.

Referring to FIGS. 5 and 10, as shown there is no object between the X-ray radiator 520 and the detector 530. When the lamp 524 is turned on, light from the lamp is emitted through the irradiation window 525 of the collimator 523. Due to the irradiation region 590 of light from the lamp 524, an image IM200 of the irradiation window 525 may be formed on the detector 530. The image of the irradiation window 525 formed on the detector 530 may be referred to as "irradiation window image IM200."

The image acquirer 510 may acquire a detector image by imaging the detector 530. In this case, the irradiation window image IM200 may be formed on the detector 530. Therefore, the detector image acquired by the image acquirer 510 may include an image area corresponding to the irradiation window image IM200.

Figure 11:
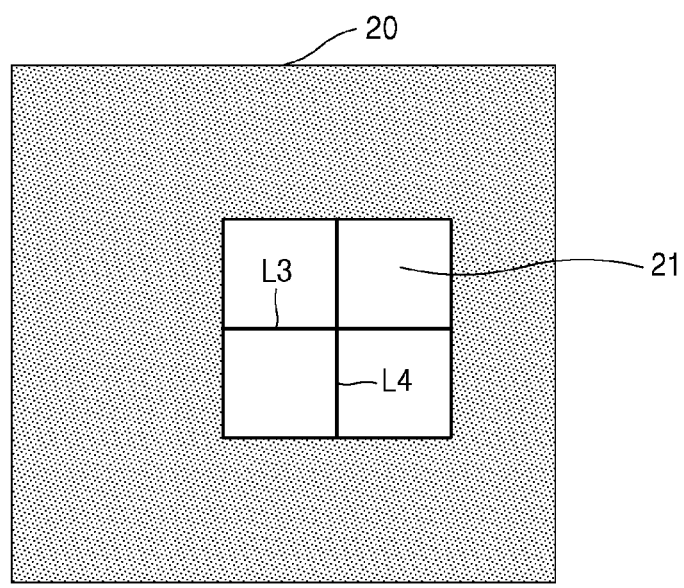
FIG. 11 is a diagram showing a detector image acquired by the X-ray apparatus of FIG. 10, according to an exemplary embodiment.

FIG. 11 is a diagram showing an example of a detector image 20 acquired by the X-ray apparatus 500 of FIG. 10, according to an exemplary embodiment.

Referring to FIGS. 10 and 11, the detector image 20 includes an image area 21 corresponding to the irradiation window image IM200 formed on the detector 530. Hereinafter, the image area 21 corresponding to the irradiation window image IM200 in the detector image 20 is referred to as "collimation region" of the detector image 20. That is, the collimation region 21 is included in the detector image 20 and corresponds to the irradiation region 590 of light emitted from the lamp 524 of the collimator 523 of FIG. 5.

The controller 550 of the X-ray apparatus 500 of FIG. 5 may detect the collimation region 21 from the detector image 20. The controller 550 of FIG. 5 may detect the collimation region 21 based on brightness information of the detector image 20, the shape of the irradiation window 525, and the like. The controller 550 of FIG. 5 may acquire the detector distance SID based on a size of the collimation region 21. The size of the collimation region 21 may correspond to the number of pixels in the collimation region 21.

Alternatively, the size of the collimation region 21 may correspond to the area size of the collimation region 21. The controller 550 of FIG. 5 may detect crossing lines L3 and L4 of the detector image 20 that correspond to the crossing lines of the irradiation window 525, and acquire the size of the collimation region 21 based on the crossing lines L3 and L4. The controller 550 of FIG. 5 may detect respective lengths of the crossing lines L3 and L4. For example, the respective lengths of the crossing lines L3 and L4 may correspond to the number of pixels that form each of the crossing lines L3 and L4. The controller 550 of FIG. 5 may multiply the respective lengths of the crossing lines L3 and L4 and thus acquire the size of the collimation region 21.

Alternatively, the size of the collimation region 21 may be estimated based on a length of one of the crossing lines L3 and L4. The controller 550 of FIG. 5 may acquire the size of the collimation region 21 based on a length of one of the crossing lines L3 and L4.

The controller 550 of FIG. 5 may acquire the detector distance SID based on the size of the collimation region 21. However, the descriptions above are only examples of a method of acquiring the size of the collimation region 21, and the method is not limited thereto.

As in the acquiring of the object distance SOD, the controller 550 of FIG. 5 may acquire the detector distance SID based on relationship information that indicates a relationship between a size of a collimation region and a detector distance.

The controller 550 of FIG. 5 may use the relationship information (e.g., the relationship information of FIG. 9) that indicates the relationship between the size of the collimation region and the object distance, which is used for the acquiring of the object distance SOD, to acquire the detector distance SID. The relationship information may be information that is acquired based on values that are measured in advance through experiments.

In FIG. 5, the image acquirer 510 of the X-ray apparatus 500 may acquire target images by imaging a target at various distances while changing a distance between the X-ray source 522 and a target. The target may be the object or the detector 530. The X-ray apparatus 500 may detect a size of a collimation region of each of the target images acquired according to distances. By doing so, the X-ray apparatus 500 may acquire the relationship information (e.g., the relationship information of FIG. 9) between the size of the collimation region and the distance between the X-ray source 522 and the target in advance. Alternatively, the X-ray apparatus 500 may receive relationship information that is acquired by another external device through experiments.

Figure 12:
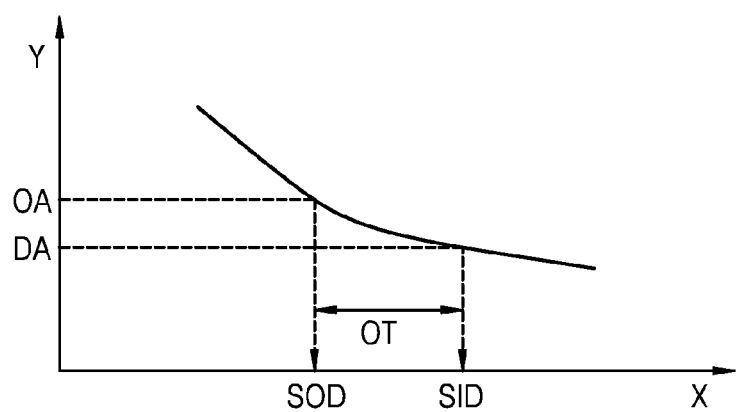
FIG. 12 is a diagram showing a relationship between an object distance, a detector distance, and a thickness of an object in the graph of FIG. 9 that shows relationship information, according to an exemplary embodiment.

FIG. 12 is a diagram showing an example of a relationship between an object distance SOD, a detector distance SID, and a thickness OT of an object in the graph of FIG. 9 that shows relationship information, according to an exemplary embodiment.

Referring to FIG. 12, when a size OA of the collimation region is acquired from the object image, the object distance SOD may be acquired based on the relationship information. Likewise, when a size DA of the collimation region of the detector image is acquired from the detector image, the detector distance SID may be acquired. The object thickness OT may be acquired based on a difference between the detector distance SID and the object distance SOD.

As described above, the controller 550 of FIG. 5 may acquire the detector distance SID by using a method similar to the method of acquiring the object distance SOD. However, this is only an exemplary embodiment of the method of acquiring the detector distance SID. The controller 550 of FIG. 5 may acquire the detector distance SID in various ways. For example, a detector may be coupled to a receptor such as a table type receptor or a stand type receptor. An X-ray apparatus may adjust or automatically acquire a distance between an X-ray source and the receptor. In this case, the X-ray apparatus may acquire the detector distance SID by using a method different from the method of acquiring the object distance SOD.

Figure 13:
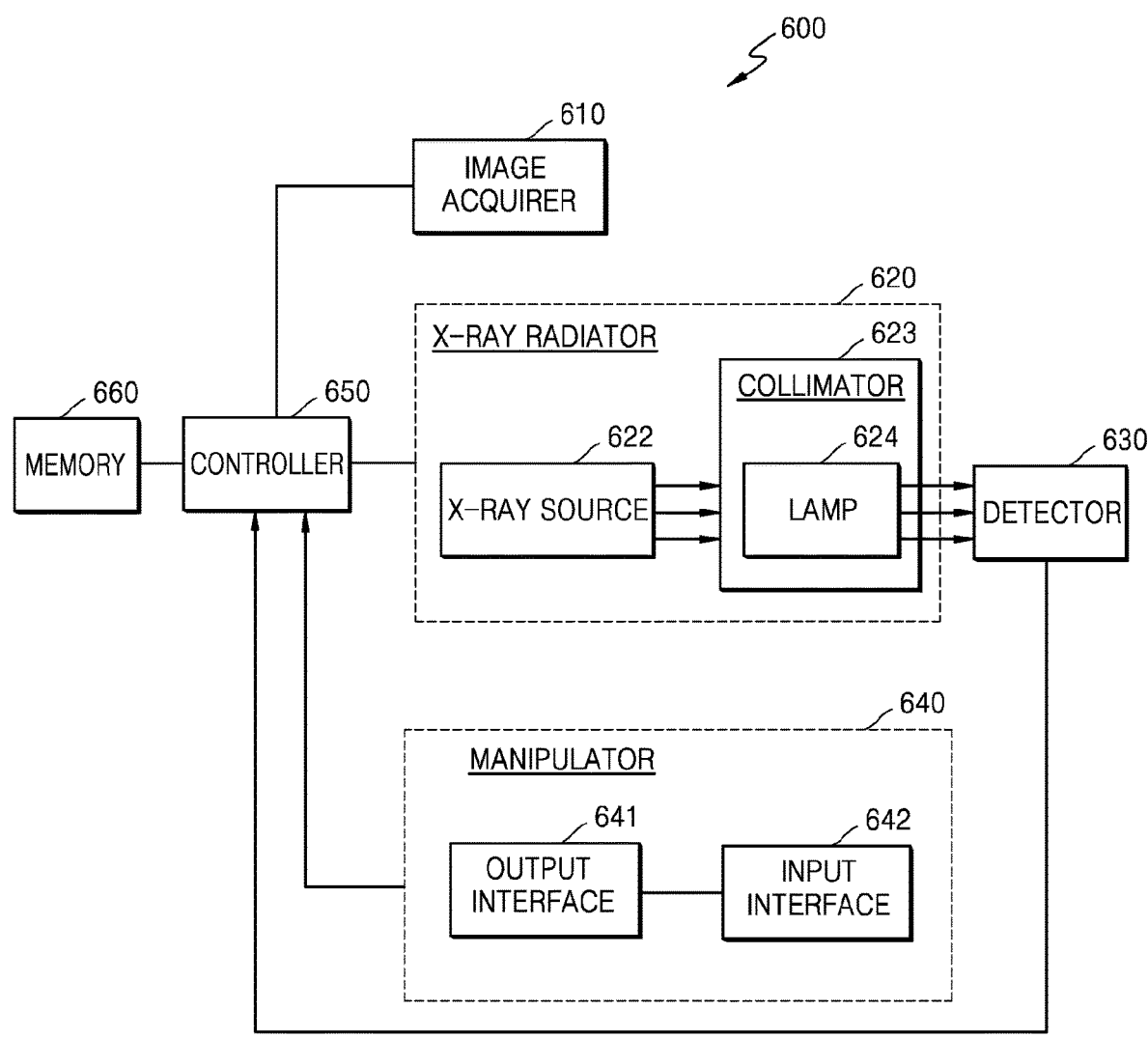
FIG. 13 is a block diagram of an X-ray apparatus, according to an exemplary embodiment.

FIG. 13 is a block diagram of an example of an X-ray apparatus 600, according to an exemplary embodiment. The X-ray apparatus 600 of FIG. 13 may be another exemplary embodiment of the X-ray apparatus 500 of FIG. 5. Therefore, whether or not described below, the above-described features may be included in the X-ray apparatus 600 of FIG. 13.

Referring to FIG. 13, the X-ray apparatus 600 includes an image acquirer 610, an X-ray radiator 620, and a controller 650. The X-ray radiator 620 may include an X-ray source 622 and a collimator 623. The collimator 623 includes a lamp 624. The X-ray apparatus 600 may further include a detector 630, a manipulator 640, and a memory 660. The manipulator 640 may include an output interface 641 and an input interface 642.

The image acquirer 610 may acquire an object image by imaging an object while the lamp 624 is turned on.

The controller 650 may acquire an object distance, which is a distance between the X-ray source 622 and the object, based on the object image acquired by the image acquirer 610. The controller 650 may detect a collimation region from the object image, and acquire the object distance based on a size of the collimation region. The controller 650 may acquire the object distance based on information stored in the memory 660, that is, information about a relationship between the size of the collimation region and a target distance which is a distance between an X-ray source 622 and a target. The target may be the object or the detector 630. The controller 650 may acquire an object thickness based on the object distance and a detector distance, which is a distance between the X-ray source 622 and the detector 630.

Also, based on the object thickness, the controller 650 may acquire an irradiation condition that is information related to an X-ray radiation amount of the X-ray source 622. The irradiation condition may refer to information that may affect the X-ray radiation amount. For example, the irradiation condition may include a tube voltage, tube current, and an X-ray radiation time of the X-ray source 622.

The irradiation condition may be thickness information based on a thickness of the object. The thickness information may include the thickness of the object, or a degree of thickness of the object based on the thickness of the object. An example of the degree of the thickness may include obesity. An appropriate amount of X-rays may increase as the thickness of the object increases. Therefore, the irradiation condition may include the thickness information.

Alternatively, the irradiation condition may be radiation amount information related to an X-ray radiation amount. The radiation amount information may include an X-ray radiation amount, power or voltage necessary for irradiating X-rays according to the X-ray radiation amount, and the like.

As described above, the irradiation condition may include at least one of the thickness information and the irradiation amount information.

The memory 660 may store information necessary for operations and controlling of the X-ray apparatus 600. The memory 660 may store first relationship information (e.g., the relationship information of FIG. 9) that indicates a relationship between the size of the collimation region and the target distance. Also, the memory 660 may further store second relationship information that indicates a relationship between the thickness of the object and the X-ray radiation amount.

The output interface 641 may output the irradiation condition related to the X-ray radiation amount.

The user may input X-ray setting information for setting the X-ray radiation amount via the input interface 642. The user may see the irradiation condition that is output on the output interface 641, and then input the X-ray setting information. The X-ray setting information may include an X-ray radiation amount, power or voltage necessary to irradiate X-rays according to the X-ray radiation amount, and the like. That is, the X-ray setting information may include the same information as the irradiation condition. However, the irradiation condition is output via the output interface 641, whereas the X-ray setting information is input by the user via the input interface 642.

When the user sets the X-ray radiation amount, the X-ray source 622 may emit X-rays according to the set X-ray radiation amount.

Figure 14:
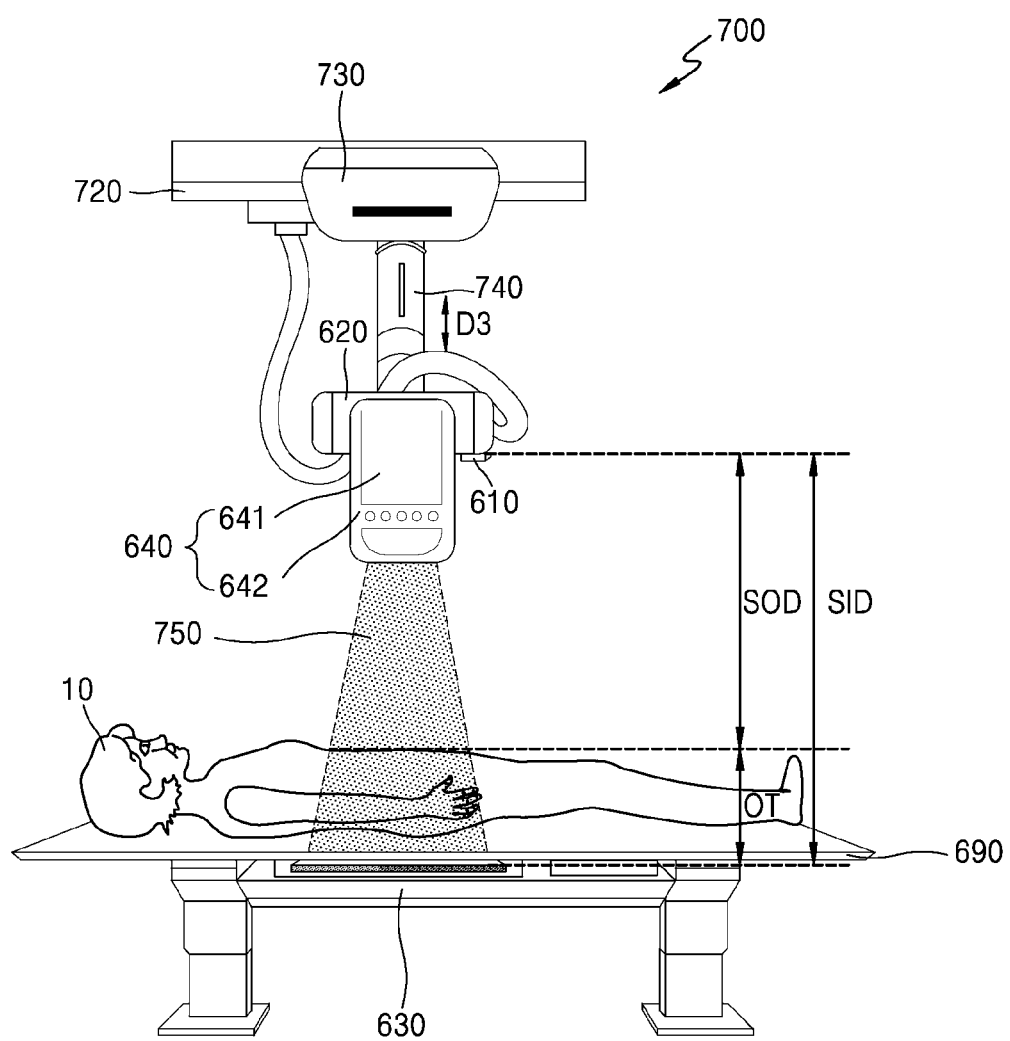
FIG. 14 is a diagram of an X-ray apparatus, according to an exemplary embodiment.

FIG. 14 is a diagram of an example of an X-ray apparatus 700, according to an exemplary embodiment. The X-ray apparatus 700 of FIG. 14 may be another exemplary embodiment of the X-ray apparatus 600 of FIG. 13. Therefore, whether or not described below, the above-described features may also be applied to the X-ray apparatus 700 of FIG. 14. Components included in the X-ray apparatus 700 of FIG. 14 that are the same as those of the X-ray apparatus 600 of FIG. 13 use the same reference numerals as those used in FIG. 13, and a repeated description thereof will be omitted. Also, the components of FIG. 13 that are not illustrated in FIG. 14 may be included in the X-ray apparatus 700 of FIG. 14.

Referring to FIGS. 13 and 14, the example X-ray apparatus 700 includes a guide rail 720, a moving carriage 730, and a post frame 740 for moving the X-ray radiator 620. Although not illustrated in FIG. 14, the X-ray radiator 620 includes the X-ray source 622 and the collimator 623 including the lamp 624, as in FIG. 13.

Although the detector 630 of FIG. 14 is illustrated as being coupled to a table type receptor 690, the detector 630 may also be coupled to a stand type receptor. Alternatively, the detector 630 may be a portable detector that is not coupled to any receptor and located at any desired location.

When the lamp 624 of the collimator 623 in the X-ray radiator 620 is turned on, light from the lamp 524 is radiated in a light irradiation region 750. The image acquirer 610 may acquire an object image by imaging the object 10. The controller 650 may acquire an object distance SOD based on the object image. The controller 650 may acquire an object thickness OT based on a detector distance SID and the object distance SOD.

The controller 650 may acquire the detector distance SID by using various methods.

For example, the controller 650 may acquire the detector distance SID based on a moving distance of the post frame 740. The guide rail 720 may be installed at a ceiling of an examination room. A height of the guide rail 720 and a height of the table type receptor 690 may be fixed. A length of the post frame 740 may increase or decrease in the third direction D3. Therefore, the controller 650 may acquire the detector distance SID when a moving distance of the post frame 740 is acquired. This example may not only be applied to a case of the detector 630 coupled to the table type receptor 690 shown in FIG. 14, but also be applied to a detector coupled to a stand type receptor.

As another example, the controller 650 may acquire the detector distance SID according to a selection of the user. The user may input distance setting information for setting the detector distance SID via the input interface 642. The controller 650 may move the post frame 740 according to the input of the user to move the X-ray radiator 620 to a location corresponding to the detector distance SID that is set. The distance setting information that is input to the input interface 642 may be the detector distance SID that the user desires, but is not limited thereto. For example, the distance setting information that is input to the input interface 642 may include an initialization instruction or an imaging preparation instruction. The detector distance SID that corresponds to the initialization instruction or the imaging preparation instruction may be a preset value. According to the initialization instruction or the imaging preparation instruction, the X-ray radiator 620 may be moved to a location that corresponds to the detector distance SID that is preset. This example may also be applied to the case of the detector 630 coupled to the table type receptor 690 as well as the detector coupled to the stand type receptor.

In some exemplary embodiments, as described above, controller 650 may acquire the detector distance SID by using a method similar to the method of acquiring the object distance SOD. This will be described with reference to FIG. 15.

Figure 15:
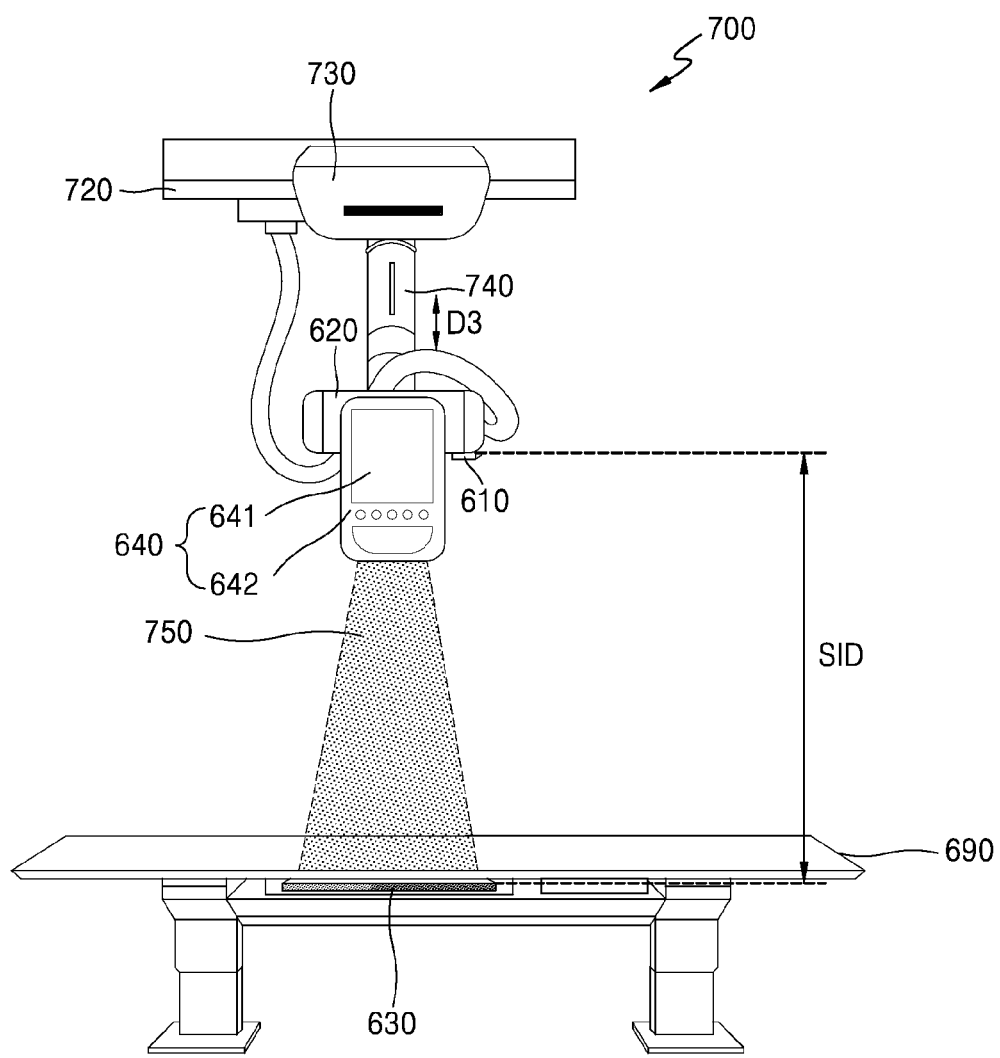
FIG. 15 is a diagram for describing acquiring of a detector distance by the X-ray apparatus of FIG. 14, according to an exemplary embodiment.

FIG. 15 is a diagram for describing an example of acquiring of a detector distance SID by the X-ray apparatus 700 of FIG. 14, according to an exemplary embodiment.

Referring to FIGS. 13 and 15, as shown there is no object between the X-ray radiator 620 and the detector 630. The image acquirer 610 may acquire a detector image by imaging the detector 630 while the lamp 624 is turned on. The image acquirer 610 of FIG. 15 may acquire the detector image by imaging a receptor 690 that is coupled to the detector 630.

The controller 650 may acquire a detector distance SID based on the detector image acquired by the image acquirer 610. The detector distance SID is a distance between the X-ray source 622 and the detector 630. A method of acquiring the detector distance SID based on the detector image may be applied to not only the detector 630 coupled to the table type receptor 690 as shown in FIG. 15, but also a detector that is coupled to a stand type receptor. Alternatively, the method may be applied to a portable detector that may be located at any desired location.

After acquiring the detector distance SID based on the detector image, the controller 650 may adjust the acquired detector distance SID again. For example, a desired distance between the X-ray source 622 and the detector 530 selected by the user may be 100 cm, and the detector distance SID acquired by the controller 650 may be 80 cm. In this case, the controller 650 may move the post frame 740 upward by 20 cm in the third direction D3.

As described above, the controller 650 may acquire an irradiation condition based on an object thickness OT that is acquired based on an object distance SOD and the detector distance SID. The irradiation condition may be information related to an X-ray radiation amount of the X-ray source 622. The output interface 641 may output the irradiation condition.

Figure 16:
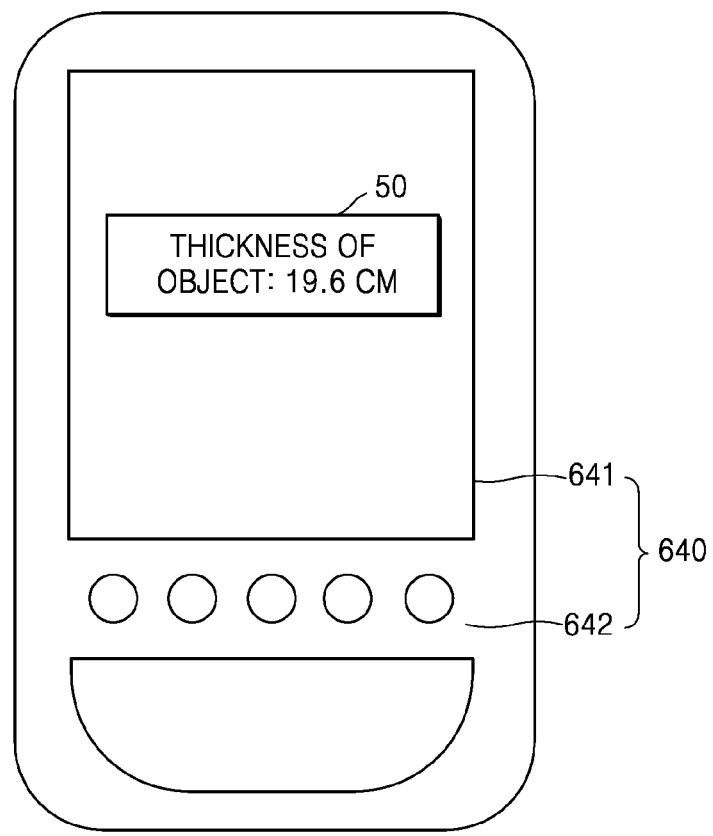
FIGS. 16 to 18 are diagrams of irradiation conditions that are output on a manipulator of the X-ray apparatus of FIG. 13, according to an exemplary embodiment.
Figure 17:
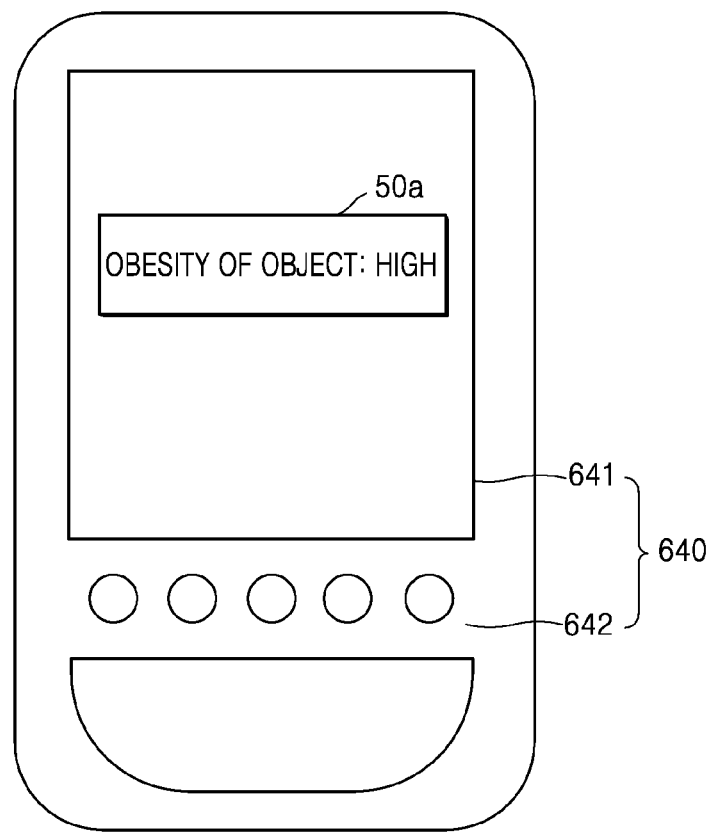
Figure 18:
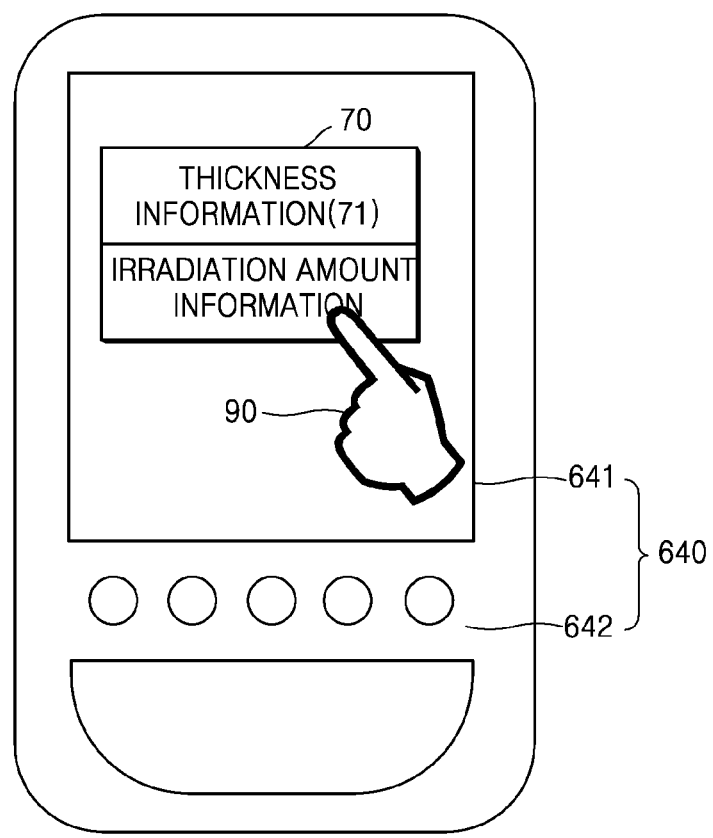

FIGS. 16 to 18 are diagrams of examples of irradiation conditions that may be output on the manipulator 640 of FIG. 13, according to an exemplary embodiment. The manipulator 640 includes the output interface 641 and the input interface 642. Although FIGS. 16 to 18 illustrate that the output interface 641 and the input interface 642 in the manipulator 640 are spaced apart, the output interface 641 and the input interface 642 are not limited thereto. The input interface 642 or a portion of the input interface 642 may be provided in the output interface 641. For example, when the input interface 642 includes a touch screen, the touch screen may be provided in the output interface 641.

Referring to FIG. 16, an irradiation condition 50 that is output on the output interface 641 may be a thickness of an object. The irradiation condition 50 may be output in text and numbers, for example, "THICKNESS OF OBJECT: 19.6 CM" as shown in FIG. 16.

Referring to FIG. 17, an irradiation condition 50a that is output on the output interface 641 may be obesity of the object. For example, the controller 650 of FIG. 13 may acquire the obesity of the object based on an object thickness. The obesity may be classified into a plurality of levels, such as "high, intermediate, and low." For example, the irradiation condition 50a may be output in text, "OBESITY OF OBJECT: HIGH" as shown in FIG. 17.

FIGS. 16 and 17 are only examples of when the irradiation conditions 50 and 50a on the output interface 641 correspond to thickness information. The output interface

641 may output the irradiation condition in various ways such that the user may recognize the thickness of the object, the degree of the thickness.

The user may input X-ray setting information for setting an X-ray radiation amount via the input interface 642 of FIGS. 16 and 17. The user may see the irradiation conditions 50 and 50a via the output interface 641, and then input the X-ray setting information. For example, when the user determines that the thickness of the object is high based on the thickness information output via the irradiation conditions 50 and 50a, the user may input the X-ray setting information such that the X-ray radiation amount increases.

Referring to FIG. 18, an irradiation condition 70 output on the output interface 641 may include at least one of thickness information 71 and radiation amount information 72. The radiation amount information 72 may be related to the X-ray radiation amount. The radiation amount information 72 may include the X-ray radiation amount, power or voltage necessary for irradiating X-rays according to the X-ray radiation amount, and the like. For example, the irradiation condition may include a tube voltage, tube current, and an X-ray radiation time of an X-ray source.

The user may input the X-ray setting information for setting the X-ray radiation amount via the input interface 642. The user may see the irradiation condition 70 via the output interface 641, and then input the X-ray setting information.

As shown in FIG. 18, the input interface 642 may include a touch screen, and a user 90 may input the X-ray setting information by touching the radiation amount information 72 in the irradiation condition 70 that is displayed on the output interface 641. For example, the user 90 may input the X-ray setting information by approving the output radiation amount information 72 or readjusting the radiation amount information 72. However, FIG. 18 is only an example of inputting the X-ray setting information. The method of inputting the X-ray setting information may be modified in various ways.

Referring to FIG. 13, the memory 660 of the X-ray apparatus 600 may store first relationship information (e.g., the relationship information of FIG. 9) that indicates a relationship between a size of a collimation region and a target distance. Also, the memory 660 may further store second relationship information that indicates a relationship between the thickness of the object and the X-ray radiation amount.

FIG. 19 is an example table of first relationship information 40 that may be stored in the memory 660 of the X-ray apparatus 600 of FIG. 13, according to an exemplary embodiment.

Referring to FIG. 19, the first relationship information 40 may be table type information in which an SID 41, which indicates distance information between an X-ray source and a target, is matched with a region size 42, which indicates size information of a collimation region. In FIG. 19, the target may be a detector. The first relationship information 40 may store relationships between detector distances SID and respective sizes of collimation regions in a detector image. That is, when the detector distance SID is a 'first distance,' the detector image is acquired and 'first size' is acquired as a size of a collimation region in the detector image. Accordingly, the first relationship information 40 may be acquired through experiments.

Here, it is assumed that the controller 650 of the X-ray apparatus 600 of FIG. 13 detects a size of a collimation region in an object image or a detector image as 'second size.' The controller 650 may acquire that an object distance or a detector distance is a 'second distance' based on the first relationship information 40 stored in the memory 660.

FIG. 19 is only an example of the first relationship information 40. As another example, the first relationship information 40 stored in the memory 660 of FIG. 13 may be a relation formula of the x-axis and the y-axis in the graph as in FIG. 9.

FIG. 20 is an example of a table of second relationship information 60 that may be stored in the memory 660 of the X-ray apparatus 600 of FIG. 13, according to an exemplary embodiment.

Referring to FIG. 20, the second relationship information 60 may be a relationship between thickness information 61 acquired based on a thickness of an object and an irradiation condition 62 of an X-ray source. The thickness information 61 and the irradiation condition 62 of FIG. 20 are only examples. The thickness information 61 may include the thickness of the object, a thickness range of the object, and a degree of thickness of the object. The irradiation condition 62 may include an X-ray radiation amount, power or voltage necessary for irradiating X-rays according to the X-ray radiation amount, and the like. For example, the irradiation condition may include a tube voltage, tube current, and an X-ray radiation time of an X-ray source.

Here, it is assumed that the controller 650 of the X-ray apparatus 600 of FIG. 13 detects the thickness of the object as 'third thickness.' The controller 650 may acquire that radiation amount information 62 is 'third radiation amount' based on the second relationship information 60 stored in the memory 660.

The output interface 641 may output the irradiation condition that includes at least one of the thickness information 61 and the radiation amount information 62. The user may input X-ray setting information via the input interface 642.

The X-ray source 622 may radiate X-rays according to an X-ray radiation amount that is set by the user.

However, the first relationship information 40 of FIG. 19 stored in the memory 660 may only apply when a size of the irradiation window 525 of FIG. 6 of the collimator 623 is limited to a specific size. The size of the irradiation window 525 of FIG. 6 may be adjusted by using the shutter 526. However, due to a limit of the memory 660, the first relationship information 40 may include respective sizes of collimation regions according to target distances, which are acquired through experiments only when the size of the irradiation window 525 of FIG. 6 is specified.

Therefore, in some exemplary embodiments the collimator 623 may adjust the size of the irradiation window 525 of FIG. 6 to a first size while the object is being imaged. The first size may be a certain size at which the first relationship information is applied. Next, the collimator 623 may adjust the size of the irradiation window 525 of FIG. 6 to a second size while the X-ray source 622 radiates X-rays. The second size may be selected by the user. Therefore, the irradiation window 525 of FIG. 6 may have different sizes while the object is imaged and while the object is captured by using X-rays.

As described above, according to an exemplary embodiment, the X-ray apparatus 600 may acquire the thickness of the object based on the object image. Also, the X-ray apparatus 600 may acquire information related to the X-ray radiation amount, i.e., the irradiation condition, based on the thickness of the object, and output the irradiation condition. Accordingly, the user may set the X-ray radiation amount of the X-ray source 622 that is appropriate for the object thickness by using the output irradiation condition. That is, according to an exemplary embodiment, the X-ray apparatus 600 may automatically detect the thickness of the object so as to guide the user to set the X-ray radiation amount that is appropriate for the thickness of the object. Thus, the user may use the X-ray apparatus more conveniently.

The X-ray apparatus 600 may detect a collimation region from the object image to acquire the thickness of the object.

Figure 21:
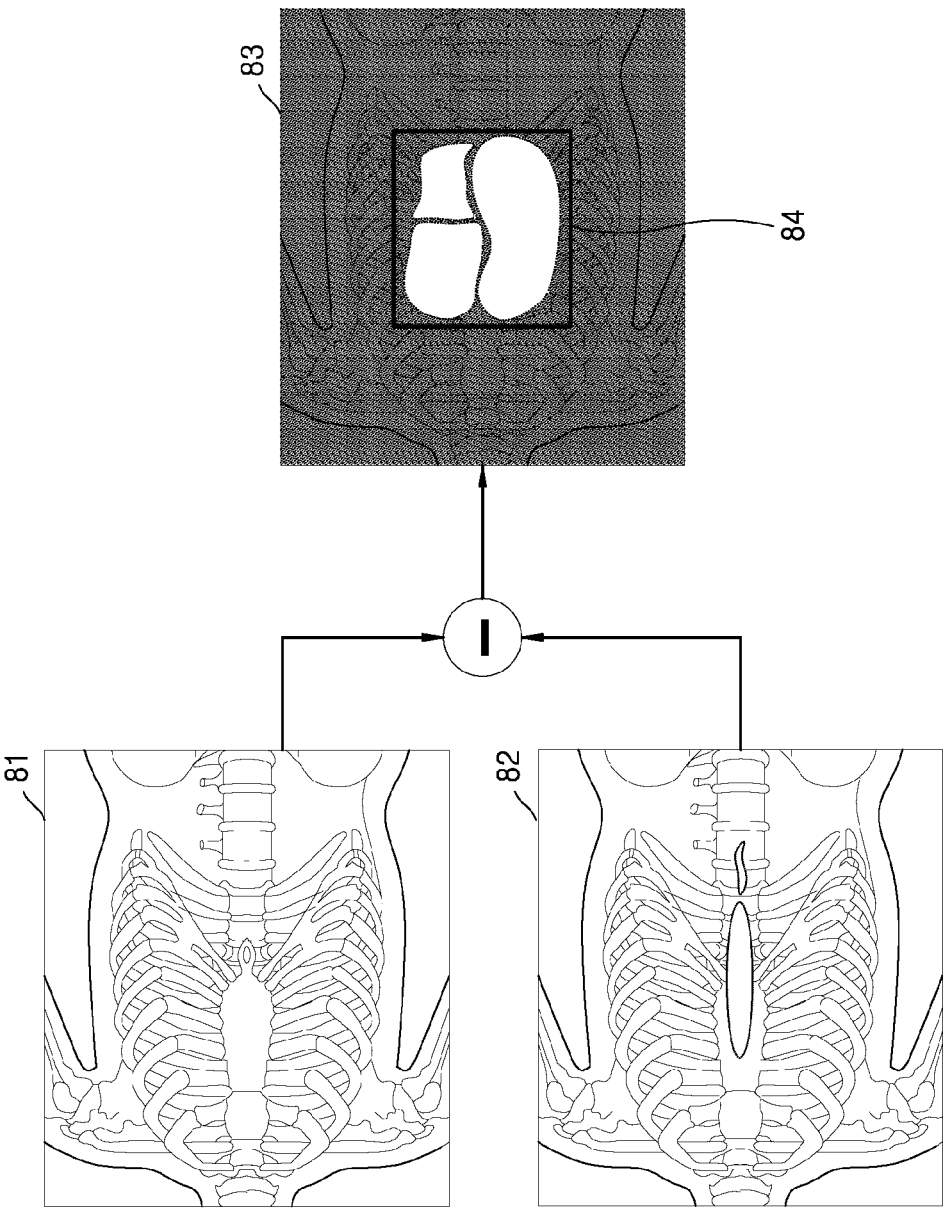
FIG. 21 is a diagram for describing acquiring of a collimation region in an object image by using the X-ray apparatus of FIG. 6, according to an exemplary embodiment.

FIG. 21 is a diagram for describing an example of acquiring of a collimation region in an object image by using the X-ray apparatus 600 of FIG. 6, according to an exemplary embodiment.

Referring to FIGS. 13 and 21, the image acquirer 610 may acquire a first object image 81 by imaging an object while the lamp 624 is turned off. Also, the image acquirer 610 may acquire a second object image 82 by imaging the same object while the lamp 624 is turned on. FIG. 21 is an example in which the object is a phantom, but exemplary embodiments are not limited thereto.

The controller 650 may acquire a difference image 83 by performing subtraction on the first object image 81 and the second object image 82. The controller 650 may detect a collimation region 84 from the difference image 83. In the difference image 83, an area other than the collimation region 84, i.e., a peripheral area may have very low brightness. The peripheral area may be substantially removed by subtraction because respective peripheral areas of the first and second object images 81 and 82 have almost no difference in brightness. In the difference image 83, because respective areas of the first and second object images 81 and 82 corresponding to the collimation region 84 have different brightness, brightness of the collimation region 84 may be increased by performing subtraction.

When a surrounding environment of the X-ray apparatus 600 is bright, the brightness of the collimation region 84 in the second object image 82 may be indifferent from that of the peripheral area. In this case, the controller 650 may detect the collimation region 84 from the difference image 83 based on not only the second object image 82 but also the first object image 81.

The controller 650 may monochromatize the first and second object images 81 and 82. For example, through image processing, the controller 650 may remove color information from the first and second object images 81 and 82 so that only bright information remains. Next, the controller 650 may acquire the difference image 83 from a monochromatized first object image and a monochromatized second object. Also, in order to detect the collimation region 84, the controller 650 may perform an additional image processing on the difference image 83, for example, thresholding or filtering. Also, when the irradiation window 525 of FIG. 6 is quadrilateral-shaped, the controller 650 may detect the collimation region 84 by using a quadrilateral pattern recognition algorithm.

FIG. 21 shows only an exemplary embodiment of a method of detecting a collimation region from an object image, and the method of detecting the collimation region is not limited thereto.

Heretofore, an X-ray apparatus according to an exemplary embodiment acquires an object thickness from an object image and outputs an irradiation condition. However, the exemplary embodiment may also be performed in a workstation. That is, the above-described features may also be applied to a workstation.

Figure 22:
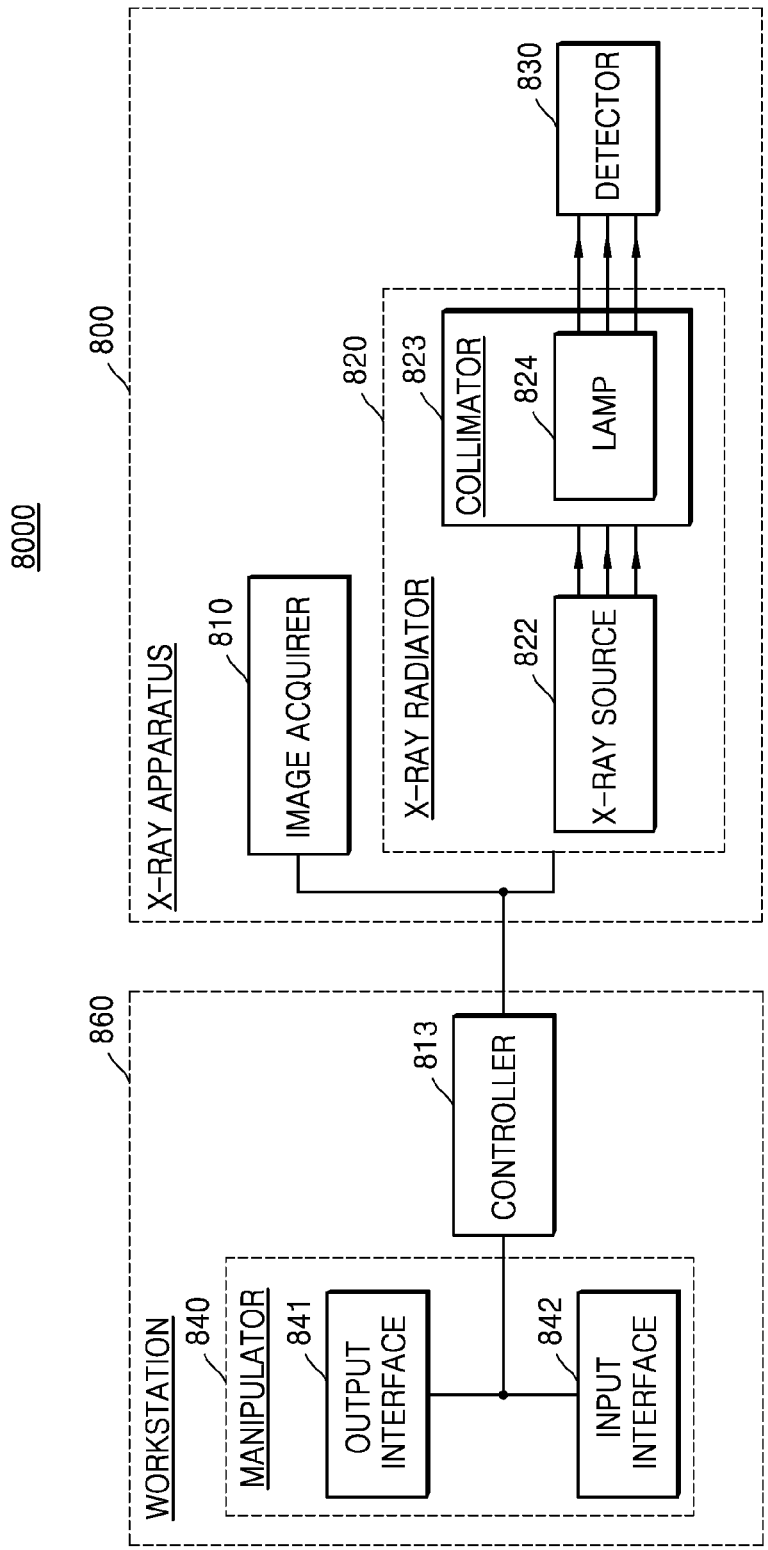
FIG. 22 is a block diagram of an X-ray system, according to an exemplary embodiment.

FIG. 22 is a block diagram of an example of an X-ray system 8000, according to an exemplary embodiment.

Referring to FIG. 22, the X-ray system 8000 includes an X-ray apparatus 800 and a workstation 860.

The example X-ray apparatus 800 includes an image acquirer 810 and an X-ray radiator 820. Also, the X-ray apparatus 800 may further include a detector 830. The X-ray radiator 820 includes an X-ray source 822 and a collimator 823. The collimator 823 includes a lamp 824. The X-ray apparatus 800 may include the features of the above-described X-ray apparatuses. Although not illustrated in FIG. 22, the X-ray apparatus 800 may also include a manipulator or a controller as in the above-described X-ray apparatuses.

The workstation 860 may include a controller 813 and a manipulator 840 that provides a user interface (UI). The manipulator 840 may include an output interface 841 and an input interface 842.

The controller 813 and the manipulator 840 of the workstation 860 may include the above-described features of the controllers and the manipulators of the X-ray apparatuses. A UI applied to the manipulator 840 of the workstation 860 may be the same as a UI applied to a manipulator of an X-ray apparatus. Therefore, a simple and intuitive UI may be provided, and the user may intuitively and conveniently operate and control the X-ray apparatus 800.

The image acquirer 810 of the X-ray apparatus 800 may acquire an object image by imaging an object while the lamp 824 is turned on.

The controller 813 of the workstation 860 may receive the object image from the X-ray apparatus 800. The workstation 860 may further include a communicator that receives the object image from the X-ray apparatus 800.

The controller 813 of the workstation 860 may turn on or off the lamp 824 of the collimator 823. Also, the controller 813 may control a size of an irradiation window of the collimator 823.

Based on the object image, the controller 813 may acquire an object distance that is a distance between the X-ray source 822 and the object. The controller 813 may acquire a thickness of the object based on the object distance and a detector distance that is a distance between the X-ray source 822 and the detector 830. Based on the thickness of the object, the controller 813 may acquire an irradiation condition that is information related to an X-ray radiation amount of the X-ray source 822.

The output interface 641 of the workstation 860 may output the irradiation condition. The user may input X-ray setting information for setting the X-ray radiation amount via the input interface 842.

The controller 813 of the workstation 860 may control the X-ray source 822 of the X-ray apparatus 800 such that the X-ray source 822 radiates X-rays according to the X-ray radiation amount. The controller 813 may adjust the size of the irradiation window of the collimator 823 to a first size while the object is being imaged, and adjust the size of the irradiation window to a second size while the X-ray source 822 radiates X-rays.

Although not illustrated in FIG. 22, the workstation 860 may further include a memory. The memory of the workstation 860 may store relationship information (e.g., the relationship information of FIG. 19) that indicates a relationship between the size of the collimation region and the target distance. Also, the memory may further store second relationship information (for example, the relationship information of FIG. 20) that indicates a relationship between the thickness of the object and the X-ray radiation amount.

Figure 23:
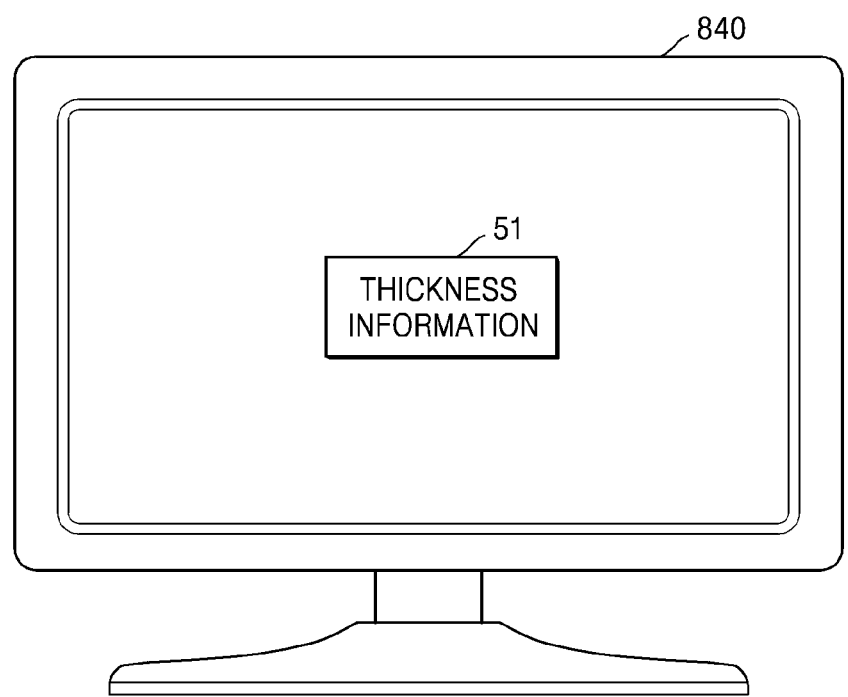
FIGS. 23 and 24 show manipulation of a workstation of FIG. 22, according to an exemplary embodiment.
Figure 24:
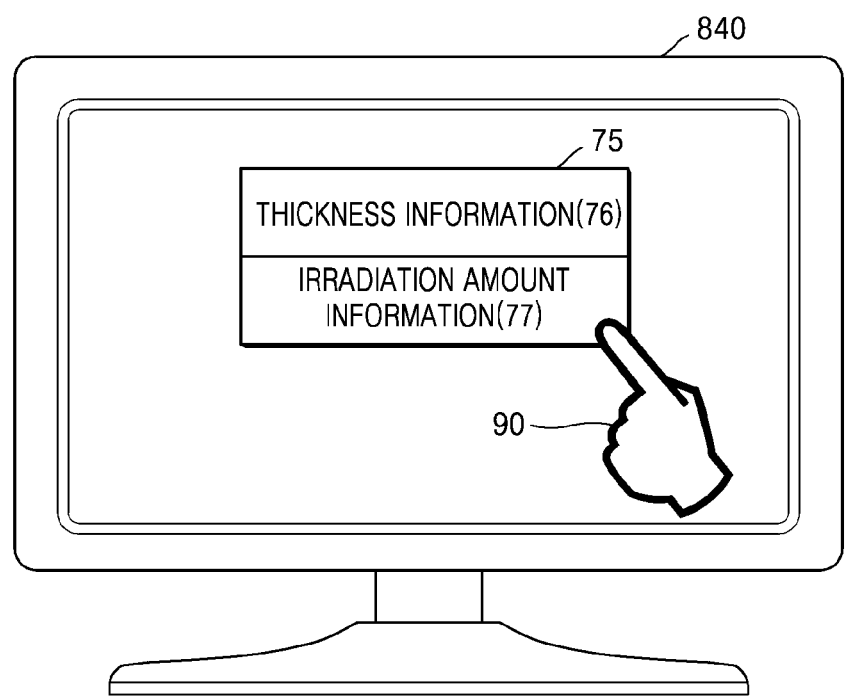

FIGS. 23 and 24 show examples of the manipulator 840 of the workstation 860 of FIG. 22, according to an exemplary embodiment.

Referring to FIG. 23, the manipulator 840 may output thickness information as an irradiation condition 51. Referring to FIG. 24, the manipulator 840 may output at least one of thickness information 76 and radiation amount information 77 as an irradiation condition 75. The user 90 may input X-ray setting information to the manipulator 840.

FIGS. 23 and 24 are only examples of the irradiation conditions that are output via the workstation 860. The irradiation conditions are not limited thereto.

Figure 25:
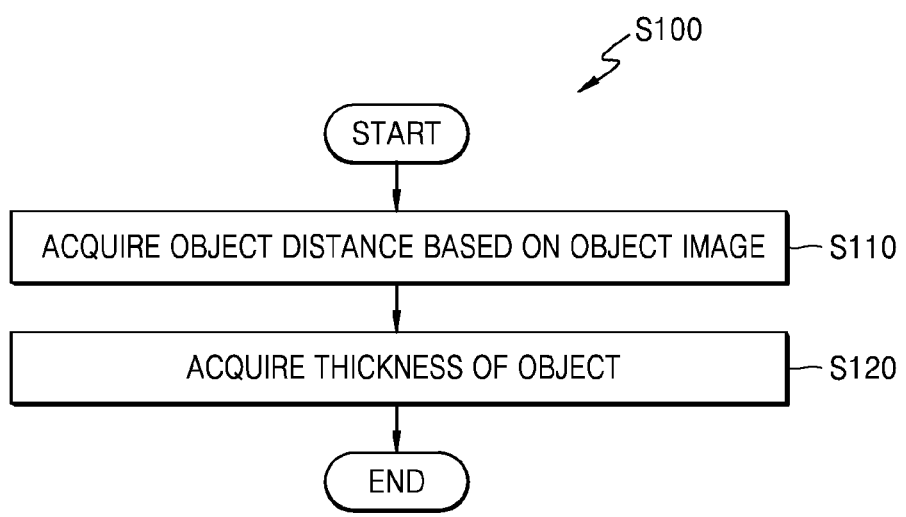
FIGS. 25 to 29 are flowcharts of an operation method of an X-ray system, according to an exemplary embodiment.

FIG. 25 is a flowchart of an example of an operation method S100 of an X-ray system, according to an exemplary embodiment.

Referring to FIG. 25, the X-ray system may acquire an object distance based on an object image that is acquired by imaging an object while a lamp of a collimator is turned on (S110). The object distance is a distance between an X-ray source and the object.

The X-ray system may acquire an object thickness based on the object distance and a detector distance that is a distance between the X-ray source and a detector (S120).

Figure 26:
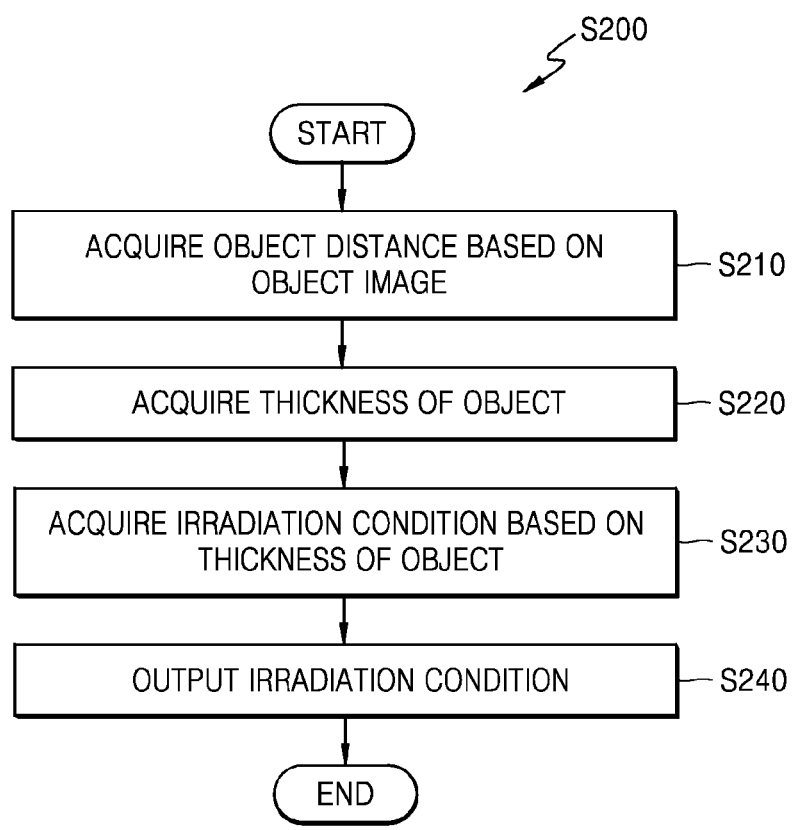

FIG. 26 is a flowchart of an example of an operation method S200 of an X-ray system, according to an exemplary embodiment.

Referring to FIG. 26, the X-ray system may acquire an object distance based on an object image (S210). The X-ray system may acquire an object thickness based on the object distance and a detector distance (S220).

Based on the object thickness, the X-ray system may acquire an irradiation condition that is information related to an X-ray radiation amount of an X-ray source (S230). The X-ray system may output the irradiation condition (S240).

Figure 27:
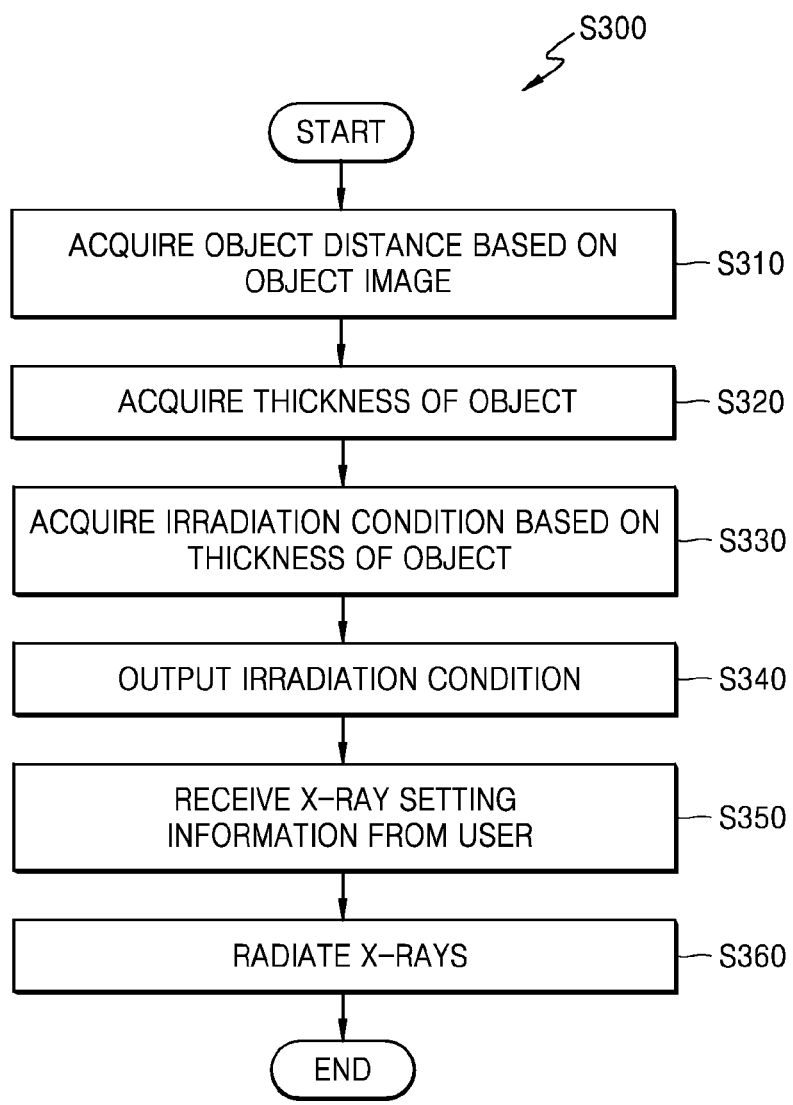

FIG. 27 is a flowchart of an example of an operation method S300 of an X-ray system, according to an exemplary embodiment.

Referring to FIG. 27, the X-ray system may acquire an object distance based on an object image (S310). The X-ray system may acquire an object thickness based on the object distance and a detector distance (S320). The X-ray system may acquire an irradiation condition based on the object thickness (S330). The X-ray system may output the irradiation condition (S340).

The X-ray system may receive X-ray setting information for setting an X-ray radiation amount from a user (S350). The X-ray system may control the X-ray source such that the X-ray source radiates X-rays according to the X-ray radiation amount (S360).

Figure 28:
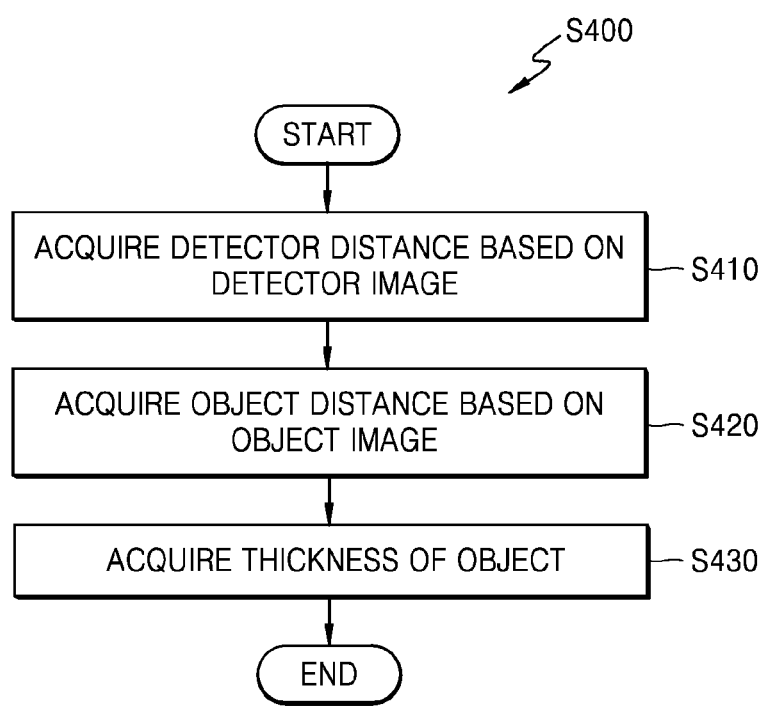

FIG. 28 is a flowchart of an example of an operation method S400 of an X-ray system, according to an exemplary embodiment.

Referring to FIG. 28, the X-ray system acquires a detector distance based on a detector image that is acquired by imaging a detector while a lamp is turned on (S410). The detector distance is a distance between an X-ray source and the detector. While imaging the detector, an object does not exist between the detector and an X-ray radiator. Also, the X-ray system may readjust the distance between the X-ray source and the detector based on the acquired detector distance.

The X-ray system may acquire an object distance based on an object image (S420). The object image may be acquired by imaging an object between the detector and the X-ray radiator while the lamp is turned on. The X-ray system may acquire an object thickness based on the object distance and the detector distance (S430).

Figure 29:
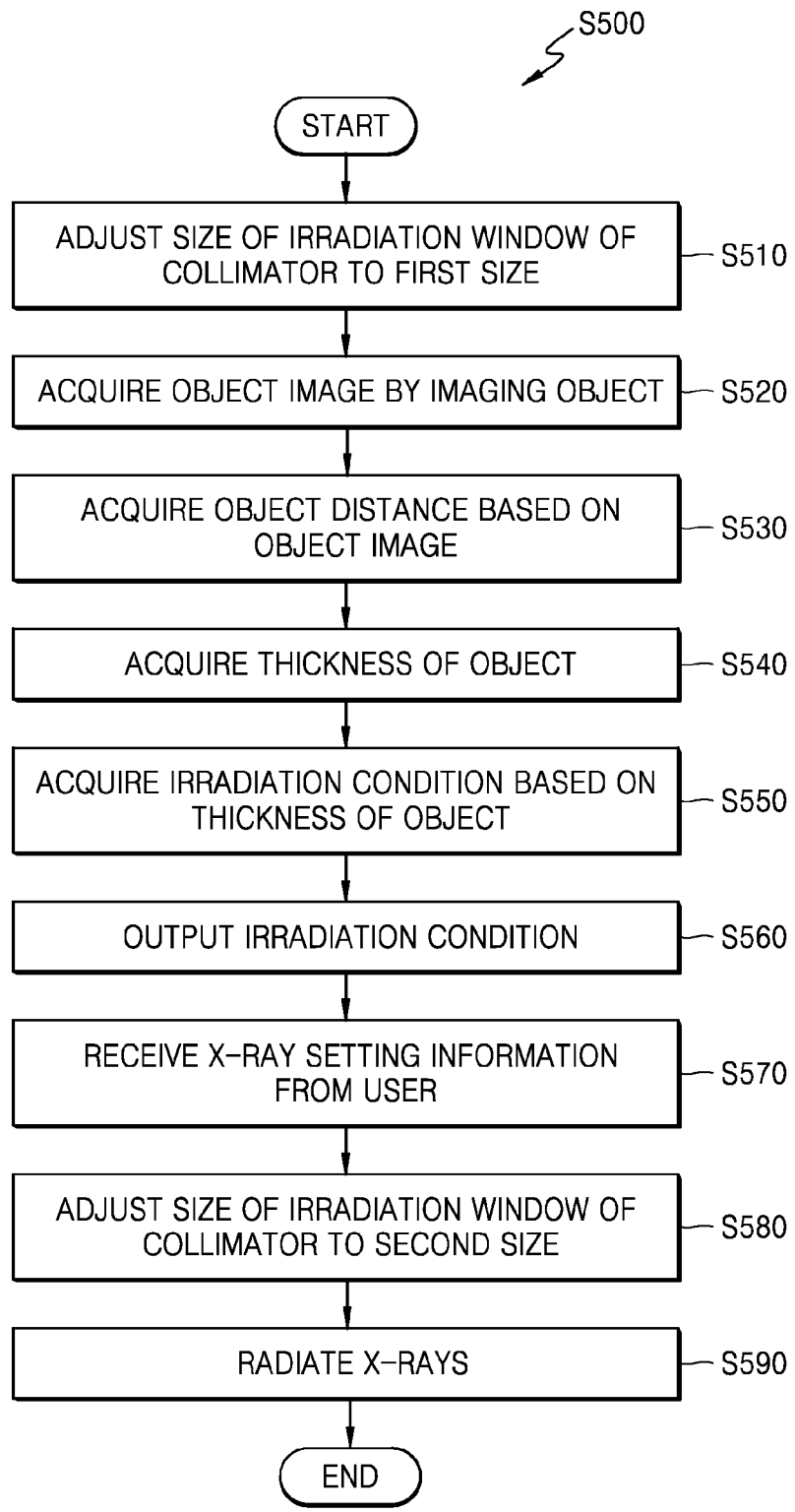

FIG. 29 is a flowchart of an example of an operation method S500 of an X-ray system, according to an exemplary embodiment.

Referring to FIG. 29, the X-ray system may adjust a size of an irradiation window of a collimator to a first size (S510). The X-ray system may acquire an object image by imaging an object while a lamp of the collimator is turned on (S520). The X-ray system may acquire an object distance based on the object image (S530). The X-ray system may acquire an object thickness based on the object distance and a detector distance (S540). The X-ray system may acquire an irradiation condition based on the object thickness (S550). The X-ray system may output the irradiation condition (S560). The X-ray system may receive X-ray setting information from a user (S570). The X-ray system may adjust the size of the irradiation window of the collimator to a second size (S580). The X-ray system may control an X-ray source such that the X-ray source radiates X-rays according to a set X-ray radiation amount (S590).

The operation methods of the X-ray systems described with reference to FIGS. 25 to 29 may be performed by an X-ray apparatus or a workstation configured to control the X-ray apparatus. Also, the above-described features may also be applied to the each step of the operation methods.

Figure 30:
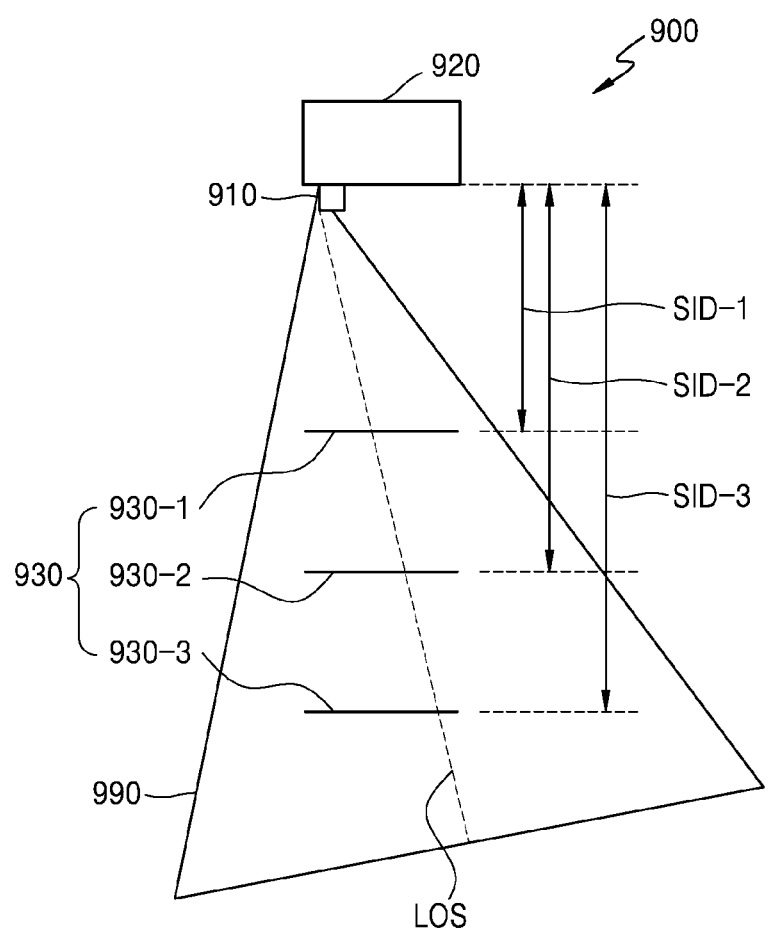
FIG. 30 is a diagram of an X-ray apparatus, according to an exemplary embodiment.

Next, referring to FIGS. 30 to 32, according to an exemplary embodiment, a method of acquiring an object distance or a detector distance based on an object image acquired by imaging an object or a detector image acquired by imaging a detector. The exemplary embodiments described below may be applied to the above-described examples in which the object distance or the detector distance is acquired based on the object image or the detector image.

FIG. 30 is a diagram of an example of an X-ray apparatus 900, according to an exemplary embodiment.

Referring to FIG. 30, the X-ray apparatus 900 may include an image acquirer 910, an X-ray radiator 920, and a detector 930. Although not illustrated in FIG. 30, the X-ray apparatus 900 may include the components included in the X-ray apparatuses described above.

930-1, 930-2, and 930-3 are reference numerals indicating the detector 930 at different positions. Also, SID-1, SID-2, and SID-3 reference numerals indicating detector distances according to the positions of the detector 930. The detector distance may refer to a distance between the detector 930 and the X-ray radiator 920. For convenience, the following terms will be used: first detector 930-1, second detector 930-2, third detector 930-3, first detector distance SID-1, second detector distance SID-2, and third detector distance SID-3.

The image acquirer 910 may be located at a boundary of a side of the X-ray radiator 920. In this case, as shown in FIG. 30, a line of sight (LOS) of the image acquirer 910 may be inclined, and a virtual camera area 990 of the image acquirer 910 may also be inclined.

Figure 31A:
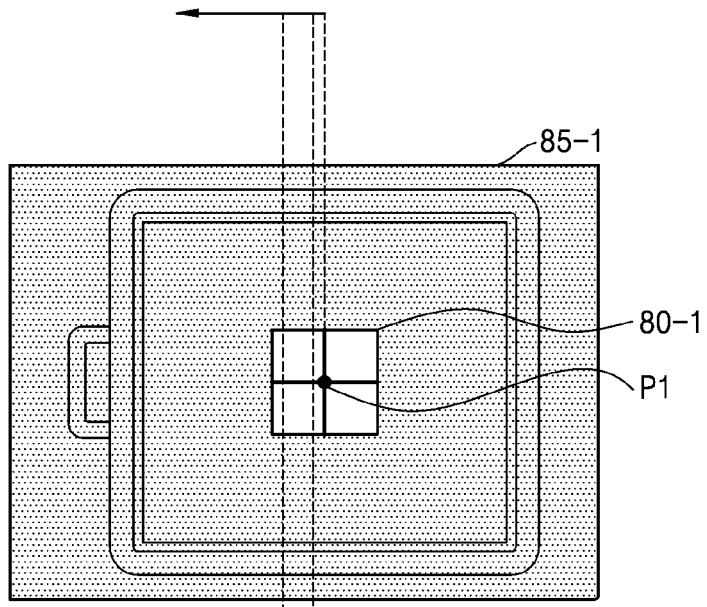
FIGS. 31A to 31C are examples of detector images acquired by an image acquirer of FIG. 30, according to exemplary embodiments.
Figure 31B:
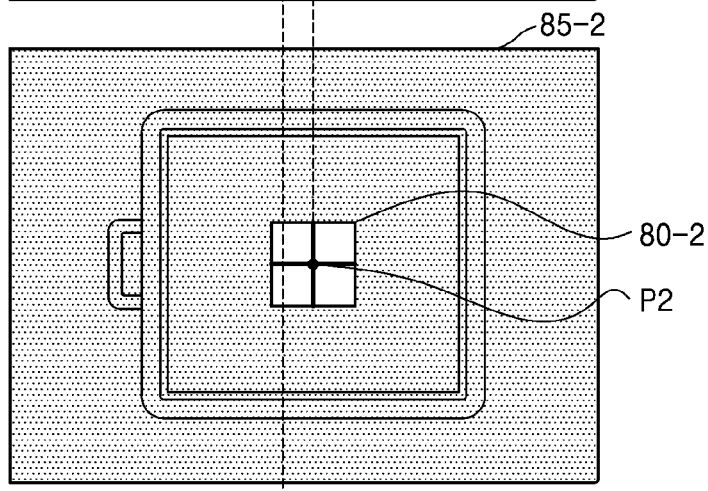
Figure 31C:
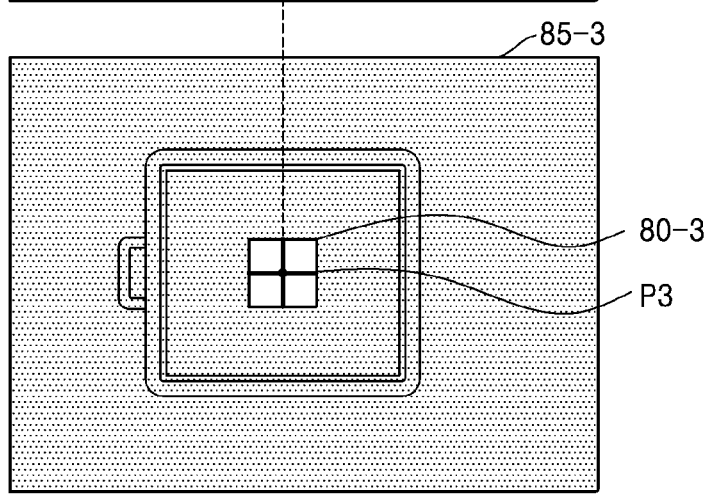

FIGS. 31A to 31C are examples of detector images acquired by the image acquirer 910 of FIG. 30.

FIG. 31A is a first detector image 85-1 acquired by capturing the first detector 930-1 of FIG. 30 at the first detector distance SID-1 from the image acquirer 910, FIG. 31B is a second detector image 85-2 acquired by capturing the second detector 930-2 at the second detector distance SID-2 from the image acquirer 910, and FIG. 31C is a third detector image 85-3 acquired by capturing the third detector 930-3 at the third detector distance SID-3 from the image acquirer 910.

Referring to FIG. 30, the first detector distance SID-1 is the shortest, and the third detector distance SID-3 is the longest. Referring to FIG. 31, a collimation region 80-1 of the first detector image 85-1 is the largest, and a collimation region 80-3 of the third detector image 85-3 is the smallest. That is, as the detector distances SID-1, SID-2, and SID-3 increase, sizes of the collimation regions 80-1, 80-2, and 80-3 decrease, respectively. Therefore, the detector distances SID-1, SID-2, and SID-3 may be acquired based on the collimation regions 80-1, 80-2, and 80-3. Details regarding this are described above.

However, when the LOS of the image acquirer 910 is inclined as shown in FIG. 30, respective locations of centers P1, P2, and P3 of the collimation regions 80-1, 80-2, and 80-3 in the detector images 85-1, 85-2, and 85-3 may change. That is, as the detector distances SID-1, SID-2, and SID-3 increase, the respective locations of the centers P1, P2, and P3 of the collimation regions 80-1, 80-2, and 80-3 in the detector images 85-1, 85-2, and 85-3 may be biased toward the left.

Therefore, the X-ray apparatus 900 may detect the respective locations of the centers P1, P2, and P3 of the collimation regions 80-1, 80-2, and 80-3 in the detector images 85-1, 85-2, and 85-3, and may acquire the detector distances SID-1, SID-2, and SID-3 based on the respective locations of the detected centers P1, P2, and P3. Also, the X-ray apparatus 900 may store, in a memory (e.g., the memory 660 of FIG. 13), a database of location-distance information that indicates a relationship between the respective locations of the centers P1, P2, and P3 of the collimation regions 80-1, 80-2, and 80-3 and the detector distances SID-1, SID-2, and SID-3. The X-ray apparatus 900 may perform experiments in advance to generate the database. For example, the X-ray apparatus 900 may acquire detector images by changing a detector distance, acquire a location of a center of a collimation region of each of the detector images, and store a relationship between the detector distance and the respective locations of the centers as location-distance information.

When a collimator of the X-ray radiator 920 of FIG. 30 includes an irradiation window 525 with crossing lines as in FIG. 6, the collimation regions 80-1, 80-2, and 80-3 of the detector images 85-1, 85-2, and 85-3 may also have crossing lines. The centers P1, P2, and P3 of the collimation regions 80-1, 80-2, and 80-3 may be the same as the center of the crossing lines. In this case, the X-ray apparatus 900 may detect the centers P1, P2, and P3 of the collimation regions 80-1, 80-2, and 80-3 by detecting respective centers of the crossing lines in the detector image 85-1, 85-2, and 85-3. However, exemplary embodiments are not limited thereto.

Figure 32A:
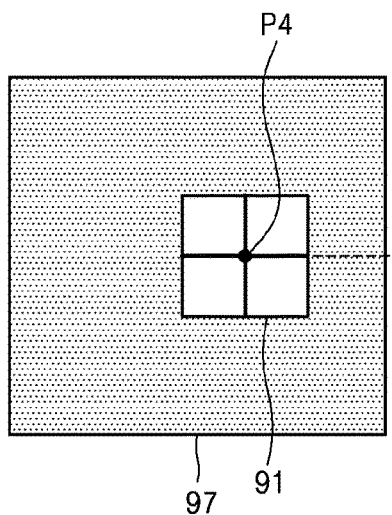
FIGS. 32A to 32C are examples of detector images and an object image, according to exemplary embodiments.
Figure 32B:
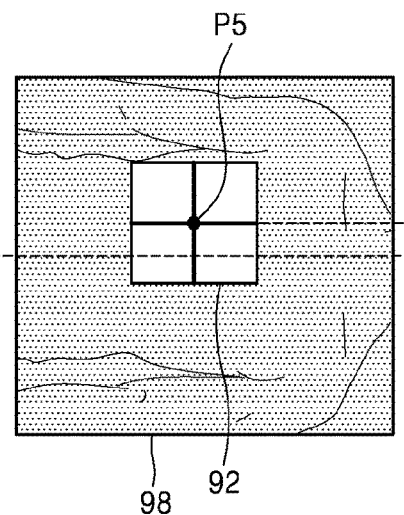
Figure 32C:
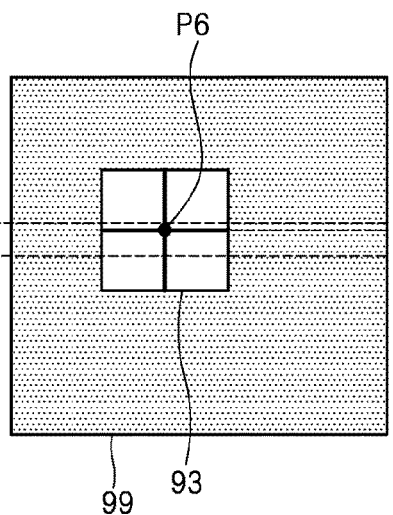

FIGS. 32A to 32C are examples of detector images and an object image.

FIGS. 32A and 32B respectively show a detector image 97 and an object image 98 having an identical detector distance. An X-ray apparatus may acquire a thickness of an object based on a difference between a location of a center P4 of a collimation region 91 of the detector image 97 and a location of a center P5 of a collimation region 92 of the object image 98.

Alternatively, the X-ray apparatus may acquire a detector distance based on a location of a center P4 of the collimation region 91 of the detector image 97, and acquire an object distance based on a location of a center P5 of the collimation region 92 of the object image 98. Then, the X-ray apparatus may acquire a difference between the detector distance and the object distance as the thickness of the object.

FIG. 32C is a detector image 99 acquired by imaging a detector at a detector distance that is the same as the object distance of FIG. 32B. For example, the detector distance of FIGS. 32A and 32B may both be 100 cm, the object distance of FIG. 32B may be 80 cm, and the detector distance of FIG. 32C may be 80 cm.

A location of a center P6 of a collimation region 93 of the detector image 99 may be substantially the same as the location of the center P5 of the collimation region 92 of the object image 98. That is, whether the target is an object or a detector, a distance from an X-ray source to the target may be acquired based on a location of a center of a collimation region in a target image.

The above-described X-ray apparatus or a workstation that controls the X-ray apparatus may acquire a target distance by detecting a center of a collimation region from a target image.

The exemplary embodiments above may be created as computer-executable programs and implemented in a general digital computer executing the programs by using a computer-readable recording medium.

The computer-readable medium may include recording media, such as magnetic storage media (e.g., ROM, floppy disks, or hard disks) and optical recording media (e.g., CD-ROMs, or DVDs).

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments. While one or more exemplary embodiments have been described with reference to the figures, it will be understood by those of ordinary skill in the art that various changes in form and details may be made therein without departing from the spirit and scope as defined by the following claims.

What is claimed is:

1. An X-ray apparatus comprising:
   an X-ray generator configured to emit X-rays to an object;
   an X-ray detector configured to detect the X-rays emitted from the X-ray generator and generate X-ray image data based on the detected X-rays;
   an image acquirer configured to acquire at least one object image by imaging the object;
   a display configured to display an X-ray image generated based on the X-ray image data; and
   at least one processor configured to obtain a thickness of the object based on the at least one object image and control the display to display an irradiation condition based on the thickness of the object;
   wherein the X-ray generator is configured to emit X-rays to the object based on the irradiation condition.

2. The X-ray apparatus of claim 1,
   wherein the image acquirer acquires at least two object images,
   wherein the at least one processor obtains the thickness of the object by comparing the at least two object images.

3. The X-ray apparatus of claim 2,
   wherein the at least one processor is further configured to identify a point from each of the at least two object images and obtain the thickness of the object by comparing the identified point of the each of the at least two object images.

4. The X-ray apparatus of claim 3,
   wherein the at least one processor obtains the thickness of the object based on a difference between a location of the identified point from each of the at least two object images.

5. The X-ray apparatus of claim 2,
   wherein the at least one processor controls the image acquirer to acquire first object image at first position and acquire second object image at second position by moving the image acquirer from the first position to the second position.

6. The X-ray apparatus of claim 1,
wherein the at least one processor identifies a point from the at least one object image, obtains a detector distance based on a location-distance information stored in a memory, and obtains the thickness of the object based on the detector distance,
wherein the location-distance information indicates a relationship between a location of the point and detector distance.

7. The X-ray apparatus of claim 1,
wherein the display displays the thickness of the object.

8. A method of operating X-ray apparatus comprising:
acquiring at least one object image by imaging an object;
obtaining a thickness of the object based on the at least one object image;
displaying an irradiation condition based on the thickness of the object;
emitting X-rays to the object based on the irradiation condition;
detecting the X-rays emitted from an X-ray generator;
generating X-ray image data based on the detected X-rays; and
displaying an X-ray image generated based on the X-ray image data.

9. A method of claim 8,
wherein the acquiring at least one object image comprises acquiring at least two object images, and
wherein the obtaining a thickness of the object comprises obtaining the thickness of the object by comparing the at least two object images.

10. A method of claim 9,
wherein the obtaining the thickness of the object comprises identifying a point from each of the at least two object images and obtaining the thickness of the object by comparing the identified point of the each of the at least two object images.

11. A method of claim 10,
wherein the obtaining the thickness of the object comprises obtaining the thickness of the object based on a difference between a location of the identified point from the each of the at least two object images.

12. A method of claim 9,
wherein the acquiring at least one object image comprises acquiring first object image at first position and acquiring second object image at second position by moving an image acquirer from the first position to the second position.

13. A method of claim 8,
wherein the obtaining the thickness of the object comprises identifying a point from the at least one object image, obtaining a detector distance based on a location-distance information stored in a memory, and obtaining the thickness of the object based on the detector distance,
wherein the location-distance information indicates a relationship between a location of the point and detector distance.

14. A method of claim 8,
wherein the displaying an irradiation condition comprises displaying the thickness of the object.

15. An X-ray apparatus comprising:
an X-ray generator configured to emit X-rays to an object;
an X-ray detector configured to detect the X-rays emitted from the X-ray generator and generate X-ray image data based on the detected X-rays;
an image acquirer configured to acquire an object image by imaging an object; and
at least one processor configured to obtain an object distance based on the object image and obtain a thickness of the object based on the object distance,
wherein the object distance is a distance between an X-ray source and the object, and,
wherein the at least one processor is further configured to determine, based on the thickness of the object, an irradiation condition, and
wherein the irradiation condition comprises information related to an X-ray radiation amount and an intensity of the X-rays radiated from the X-ray source.

16. The X-ray apparatus of claim 15,
wherein the X-ray apparatus further comprises an display configured to display at least one of the irradiation condition and the thickness of the object.

17. The X-ray apparatus of claim 15,
wherein the at least one processor identifies a point from the object image and obtains a detector distance based on a location-distance information stored in a memory, and obtains the thickness of the object based on the detector distance,
wherein the location-distance information indicates a relationship between a location of the point and detector distance.

18. A method for imaging X-ray comprising:
acquiring an object image by imaging an object;
obtaining an object distance based on the object image
obtaining a thickness of the object based on the object distance;
determining an irradiation condition based on the thickness of the object;
emitting X-rays to the object based on the irradiation condition;
detecting the X-rays emitted from an X-ray generator; and
generating X-ray image data based on the detected X-rays,
wherein the object distance is a distance between an X-ray source and the object,
wherein the irradiation condition comprises information related to an X-ray radiation amount and an intensity of the X-rays radiated from the X-ray source.

19. A method of claim 18, further comprising:
displaying at least one of the irradiation condition and the thickness of the object.

20. A method of claim 18,
wherein the obtaining the thickness of the object comprises identifying a point from the object image, obtaining a detector distance based on a location-distance information stored in a memory, and obtaining the thickness of the object based on the detector distance,
wherein the location-distance information indicates a relationship between a location of the point and detector distance.

* * * * *